(12) United States Patent
Ruebsam et al.

(10) Patent No.: US 8,129,368 B2
(45) Date of Patent: *Mar. 6, 2012

(54) 5,6-DIHYDRO-1H-PYRIDIN-2-ONE COMPOUNDS

(75) Inventors: Frank Ruebsam, San Diego, CA (US); Chinh V Tran, San Diego, CA (US); Douglas E. Murphy, San Diego, CA (US); Peggy A. Thompson, San Diego, CA (US); Peter Dragovich, San Diego, CA (US); Stephen E. Webber, San Diego, CA (US)

(73) Assignee: Anadys Pharmaceuticals, Inc., San Diego, CA (US)

( * ) Notice: Subject to any disclaimer, the term of this patent is extended or adjusted under 35 U.S.C. 154(b) by 70 days.

This patent is subject to a terminal disclaimer.

(21) Appl. No.: 12/576,739

(22) Filed: Oct. 9, 2009

(65) Prior Publication Data

US 2010/0119481 A1    May 13, 2010

Related U.S. Application Data

(60) Provisional application No. 61/104,163, filed on Oct. 9, 2008.

(51) Int. Cl.
*A61K 31/5415* (2006.01)
(52) U.S. Cl. .................... 514/223.2; 544/13
(58) Field of Classification Search ............. 544/13
See application file for complete search history.

(56) References Cited

U.S. PATENT DOCUMENTS

| 5,721,255 | A | 2/1998 | Howard et al. |
|---|---|---|---|
| 7,939,524 | B2 * | 5/2011 | Tran et al. ............. 514/223.2 |
| 2005/0075331 | A1 | 4/2005 | Pratt et al. |
| 2005/0153877 | A1 | 7/2005 | Miao et al. |
| 2006/0040927 | A1 | 2/2006 | Blake et al. |
| 2006/0189602 | A1 | 8/2006 | Zhou et al. |
| 2006/0211695 | A1 | 9/2006 | Borzilleri et al. |
| 2006/0252785 | A1 | 11/2006 | Blake et al. |
| 2008/0073982 | A1 | 3/2008 | Ono et al. |

FOREIGN PATENT DOCUMENTS

| WO | WO-01/85172 | A1 | 11/2001 |
|---|---|---|---|
| WO | WO-02/098424 | A1 | 12/2002 |
| WO | WO-03/059356 | A2 | 7/2003 |
| WO | WO-2006115221 | | 11/2006 |

OTHER PUBLICATIONS

West, Anthony R., Solid State Chemistry and its Applications, Wiley, New York, 1988, pp. 358 and 365.*
Morissette et al. "High-throughput crystallization: polymorphs, salts, co-crystals and solvates of pharmaceutical solids." 2004, Advanced Drug Delivery Reviews, 56, 275-300.*
Ruebsam et al. "Discovery of tricyclic 5,6-dihydro-1H-pyridin-2-ones as novel, potent, and orally bioavailable inhibitors of HCV NS5B polymerase." 2009, Bioorganic and Medicinial Chemistry Letters, 19, 6404-6412.*
U.S. Appl. No. 11/766,668, Ellis et al.
U.S. Appl. No. 11/898,334, Zhou et al.
U.S. Appl. No. 11/861,678, Dragovich et al.
U.S. Appl. No. 11/955,144, Tran et al.
U.S. Appl. No. 11/955,193, Ruebsam et al.
U.S. Appl. No. 11/048,933, Ruebsam et al.
U.S. Appl. No. 12/061,499, Tran et al.
U.S. Appl. No. 11/845,515, Ellis et al.
Tedesco et al., 3-(1,2,4)-benzothiadiazin-3-yl)-4-hydroxy-2(1H)-quinolinones, Potent Inhibitors of Hepatitis C Virus RNA-Dependent RNA Polymerase, J. Med. Chem. 49:971-983 (2006).
Fisyuk et al., Synthesis of 5,6-Dihydropyridin-2(1H)-ones, 1,5,6,8,8a-Hexahydroisoquinolin-3(2H)-ones and 4a,5,6,7,8,8a-Hexahydroquinolin-2(1H)-ones by Intramolecular Wittig Reaction. Molecules, Feb. 28, 2002, vol. 7, pp. 124-128.
Pogam et al., Selection and Characterization of Replicon Variants Dually Resistant to Thumb-and Palm-Binding Nonnucleoside Polymerase Inhibitors of the Hepatitis C Virus, Journal of Virology, Jun. 2006, vol. 80, No. 12, pp. 6146-6154.
International Search Report and Written Opinion, International Application No. PCT/US09/60183 dated Dec. 23, 2009.

* cited by examiner

*Primary Examiner* — James O Wilson
*Assistant Examiner* — Brian McDowell
(74) *Attorney, Agent, or Firm* — Connolly Bove Lodge & Hutz LLP

(57) ABSTRACT

The invention is directed to 5,6-dihydro-1H-pyridin-2-one compounds of formula:

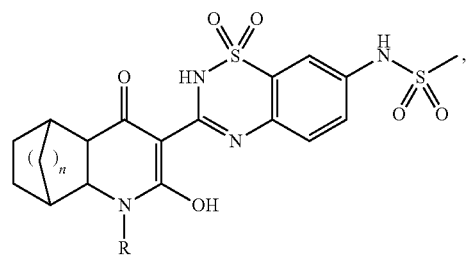

wherein R is $C_1$-$C_6$ alkyl or (Aryl)$CH_2$-,and pharmaceutical compositions containing such compounds that are useful in treating infections by hepatitis C virus.

6 Claims, No Drawings

5,6-DIHYDRO-1H-PYRIDIN-2-ONE COMPOUNDS

This application claims the benefit of U.S. Provisional Application No. 61/104,163, filed Oct. 9, 2008.

FIELD OF THE INVENTION

The invention is directed to 5,6-dihydro-1H-pyridin-2-one compounds and pharmaceutical compositions containing such compounds that are useful in treating infections by hepatitis C virus.

BACKGROUND OF THE INVENTION

Hepatitis C is a major health problem world-wide. The World Health Organization estimates that 170 million people are chronic carriers of the hepatitis C virus (HCV), with 4 million carriers in the United States alone. In the United States, HCV infection accounts for 40% of chronic liver disease and HCV disease is the most common cause for liver transplantation. HCV infection leads to a chronic infection and about 70% of persons infected will develop chronic histological changes in the liver (chronic hepatitis) with a 10-40% risk of cirrhosis and an estimated 4% lifetime risk of hepatocellular carcinoma. The CDC estimates that each year in the United States there are 35,000 new cases of HCV infection and approximately ten thousand deaths attributed to HCV disease.

The current standard of care is a pegylated interferon/ribavirin combination at a cost of approximately \$30,000/year. These drugs have difficult dosing problems and side-effects and do not achieve a sustained virological response in a significant number of diagnosed patients. Pegylated interferon treatment is associated with menacing flu-like symptoms, irritability, inability to concentrate, suicidal ideation, and leukocytopenia. Ribavirin is associated with hemolytic anemia and birth defects.

The overall response to this standard therapy is low; as approximately one third of patients do not respond. Of those who do respond, some relapse within six months of completing 6-12 months of therapy. As a consequence, the long-term response rate for all patients entering treatment is only about 50%. The relatively low response rate and the significant side-effects of current therapy anti-HCV drug treatments, coupled with the negative long term effects of chronic HCV infection, result in a continuing medical need for improved therapy. Antiviral pharmaceuticals to treat RNA virus diseases like HCV are few, and as described above are often associated with multiple adverse effects.

A number of publications have described NS5B inhibitors useful in the treatment of hepatitis C infection. See, e.g., International Publication No. WO 2008/124450 (disclosing certain 5,6-dihydro-1H-pyridin-2-one compounds); U.S. Patent Application Publication No. US 2008/0031852 (describing [1,2-b]pyridazinone compounds); U.S. Patent Application Publication No. US 2006/0189602 (disclosing certain pyridazinones); U.S. Patent Application Publication No. US 2006/0252785 (disclosing selected heterocyclics); and International Publication Nos. WO 03/059356, WO 2002/098424, and WO 01/85172 (each describing a particular class of substituted thiadiazines).

While there are, in some cases, medicines available to reduce disease symptoms, there are few drugs to effectively inhibit replication of the underlying virus. The significance and prevalence of RNA virus diseases, including but not limited to chronic infection by the hepatitis C virus, and coupled with the limited availability and effectiveness of current antiviral pharmaceuticals, have created a compelling and continuing need for new pharmaceuticals to treat these diseases.

SUMMARY OF THE INVENTION

The present invention describes novel 5,6-dihydro-1H-pyridin-2-one compounds and pharmaceutically acceptable salts thereof, which are useful in treating or preventing a hepatitis C virus infection in a patient in need thereof comprising administering to the patient a therapeutically or prophylactically effective amount of a 5,6-dihydro-1H-pyridin-2-one compound.

The invention relates to compounds selected from (1R,2S,7R,8S)—N-{3-[3-(2-Chloro-4-fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, N-{3-[(1S,2S,7R,8R)-3-(3-Chloro-4-fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, N-{3-[(2S,7R)-6-Hydroxy-3-(3-methoxy-benzyl)-4-oxo-3-aza-tricyclo[6.2.2.0$^{2,7}$]dodec-5-en-5-yl]-1,1-dioxo-1,4-dihydro-1$\lambda^6$-benzo[1,2,4]thiadiazin-7-yl}-methanesulfonamide, N-{3-[(2S,7R)-3-(2,4-Difluoro-benzyl)-6-hydroxy-4-oxo-3-aza-tricyclo[6.2.2.0$^{2,7}$]dodec-5-en-5-yl]-1,1-dioxo-1,4-dihydro-1$\lambda^6$-benzo[1,2,4]thiadiazin-7-yl}-methanesulfonamide, N-{3-[(2S,7R)-3-(2-Chloro-4-fluoro-benzyl)-6-hydroxy-4-oxo-3-aza-tricyclo[6.2.2.0$^{2,7}$]dodec-5-en-5-yl]-1,1-dioxo-1,4-dihydro-1$\lambda^6$-benzo[1,2,4]thiadiazin-7-yl}-methanesulfonamide, N-{3-[(2S,7R)-3-(2-Bromo-benzyl)-6-hydroxy-4-oxo-3-aza-tricyclo[6.2.2.0$^{2,7}$]dodec-5-en-5-yl]-1,1-dioxo-1,4-dihydro-1$\lambda^6$-benzo[1,2,4]thiadiazin-7-yl}-methanesulfonamide, N-{3-[(2S,7R)-3-(4-Fluoro-3-methoxy-benzyl)-6-hydroxy-4-oxo-3-aza-tricyclo[6.2.2.0$^{2,7}$]dodec-5-en-5-yl]-1,1-dioxo-1,4-dihydro-1$\lambda^6$-benzo[1,2,4]thiadiazin-7-yl}-methanesulfonamide, N-{3-[(2S,7R)-3-(3-Chloro-4-fluoro-benzyl)-6-hydroxy-4-oxo-3-aza-tricyclo[6.2.2.0$^{2,7}$]dodec-5-en-5-yl]-1,1-dioxo-1,4-dihydro-1$\lambda^6$-benzo[1,2,4]thiadiazin-7-yl}-methanesulfonamide, N-{3-[(2S,7R)-3-(3,3-Dimethyl-butyl)-6-hydroxy-4-oxo-3-aza-tricyclo[6.2.2.0$^{2,7}$]dodec-5-en-5-yl]-1,1-dioxo-1,4-dihydro-1$\lambda^6$-benzo[1,2,4]thiadiazin-7-yl}-methanesulfonamide, N-{3-[(2S,7R)-3-(3,4-Difluoro-benzyl)-6-hydroxy-4-oxo-3-aza-tricyclo[6.2.2.0$^{2,7}$]dodec-5-en-5-yl]-1,1-dioxo-1,4-dihydro-1$\lambda^6$-benzo[1,2,4]thiadiazin-7-yl}-methanesulfonamide, N-{3-[(2S,7R)-3-(4-Fluoro-3-methyl-benzyl)-6-hydroxy-4-oxo-3-aza-tricyclo[6.2.2.0$^{2,7}$]dodec-5-en-5-yl]-1,1-dioxo-1,4-dihydro-1$\lambda^6$-benzo[1,2,4]thiadiazin-7-yl}-methanesulfonamide, N-{3-[(2S,7R)-3-Benzyl-6-hydroxy-4-oxo-3-aza-tricyclo[6.2.2.0$^{2,7}$]dodec-5-en-5-yl]-1,1-dioxo-1,2-dihydro-1$\lambda^6$-benzo[1,2,4]thiadiazin-7-yl}-methanesulfonamide, (rac-di-exo,di-exo)-N-{3-[3-(4-Fluoro-benzyl)-6-hydroxy-4-oxo-3-aza-tetracyclo[6.3.1.0$^{2,7}$.0$^{9,11}$]dodec-5-en-5-yl]-1,1-dioxo-1,2-dihydro-1$\lambda^6$-benzo[1,2,4]thiadiazin-7-yl}-methanesulfonamide, N-{3-[(2S,7R)-3-(3-Fluoro-benzyl)-6-hydroxy-4-oxo-3-aza-tricyclo[6.2.2.0$^{2,7}$]dodec-5-en-5-yl]-1,1-dioxo-1,2-dihydro-1λ$^6$-benzo[1,2,4]thiadiazin-7-yl}-methanesulfonamide, N-{3-[(2S,7R)-3-Cyclohexylmethyl-6-hydroxy-4-oxo-3-aza-tricyclo[6.2.2.0$^{2,7}$]dodec-5-en-5-yl]-1,1-dioxo-1,2-dihydro-1λ$^6$-benzo[1,2,4]thiadiazin-7-yl}-methanesulfonamide, N-{3-[(2S,7R)-6-Hydroxy-4-oxo-3-thiophen-2-ylmethyl-3-aza-tricyclo[6.2.2.0$^{2,7}$]dodec-5-en-5-yl]-1,1-dioxo-1,2-dihydro-1λ$^6$-benzo[1,2,4]thiadiazin-7-yl}-methanesulfonamide, N-{3-[(2S,7R)-6-Hydroxy-3-(2-methyl-benzyl)-4-oxo-3-aza-tricyclo[6.2.2.0$^{2,7}$]dodec-5-en-5-yl]-1,1-dioxo-1,2-dihydro-1λ$^6$-benzo[1,2,4]thiadiazin-7-yl}-methanesulfonamide, N-{3-[(2S,7R)-6-Hydroxy-4-oxo-3-(2,3,4-trifluoro-benzyl)-3-aza-tricyclo[6.2.2.0$^{2,7}$]dodec-5-en-5-yl]-1,1-dioxo-1,2-dihydro-1λ$^6$-benzo[1,2,4]thiadiazin-7-yl}-methanesulfonamide, N-{3-[(1S,2S,7R,8R)-3-(4-Fluoro-3-methyl-benzyl)-6-hydroxy-4-oxo-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide, N-{3-[(1S,2S,7R,8R)-(3-Benzyl-6-hydroxy-4-oxo-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide, N-{3-[(1R,2S,7R,8S)-3-(3-Fluoro-benzyl)-6-hydroxy-4-oxo-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide, N-{3-[(1S,2S,7R,8R)-6-Hydroxy-4-oxo-3-(1-trifluoromethyl-cyclopropylmethyl)-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide, N-{3-[(1S,2S,7R,8R)-3-(3,4-Difluoro-benzyl)-6-hydroxy-4-oxo-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide, N-{3-[(1R,2S,7R,8S)-6-Hydroxy-4-oxo-3-(2,3,4-trifluoro-benzyl)-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide, N-{3-[(1R,2S,7R,8S)-6-Hydroxy-4-oxo-3-thiophen-3-ylmethyl-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide, N-{3-[(2S,7R)-6-Hydroxy-4-oxo-3-(2,4,5-trifluoro-benzyl)-3-aza-tricyclo[6.2.2.0$^{2,7}$]dodec-5-en-5-yl]-1,1-dioxo-1,2-dihydro-1λ$^6$-benzo[1,2,4]thiadiazin-7-yl}-methanesulfonamide, N-{3-[(1R,2S,7R,8S)-6-Hydroxy-4-oxo-3-thiophen-2-ylmethyl-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide, N-{3-[(1R,2S,7R,8S)-(3-Cyclohexylmethyl-6-hydroxy-4-oxo-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide, N-{3-[(1S,2S,7R,8R)-6-Hydroxy-3-(2-methyl-benzyl)-4-oxo-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide, and N-{3-[(1S,2S,7R,8R)-3-(3-Fluoro-benzyl)-6-hydroxy-4-oxo-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide.

In another aspect the invention is related to compounds selected from (1R,2S,7R,8S)—N-{3-[3-(2-Chloro-4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide, N-{3-[(2S,7R)-3-(2-Chloro-4-fluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide, N-{3-[(2S,7R)-3-(4-Fluoro-3-methoxy-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide, N-{3-[(2S,7R)-3-(3-Chloro-4-fluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide, N-{3-[(2S,7R)-3-(3,4-Difluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide, N-{3-[(2S,7R)-3-(4-Fluoro-3-methyl-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide, and (rac-di-exo,di-exo)-N-{3-[3-(4-Fluoro-benzyl)-6-hydroxy-4-oxo-3-aza-tetracyclo[6.3.1.0$^{2,7}$.0$^{9,11}$]dodec-5-en-5-yl]-1,1-dioxo-1,2-dihydro-1λ$^6$-benzo[1,2,4]thiadiazin-7-yl}-methanesulfonamide.

In yet another aspect the invention is related to compounds (1R,2S,7R,8S)—N-{3-[3-(2-Chloro-4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide, and N-{3-[(2S,7R)-3-(3,4-Difluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide.

The invention is also directed to pharmaceutically acceptable salts and pharmaceutically acceptable solvates of the compounds of the invention. Advantageous methods of making the compounds of the invention are also described.

In one aspect, the invention encompasses a method for treating or preventing hepatitis C virus infection in a mammal in need thereof, preferably in a human in need thereof, comprising administering to the patient a therapeutically or prophylactically effective amount of a compound of the invention. In one embodiment, the invention encompasses a method for treating or preventing hepatitis C virus infection by administering to a patient in need thereof a therapeutically or prophylactically effective amount of a compound of the invention that is an inhibitor of HCV NS5B polymerase.

In another aspect, the invention encompasses a method for treating or preventing hepatitis C virus infection in a patient in need thereof, comprising administering to the patient a therapeutically or prophylactically effective amount of a compound of the invention and a pharmaceutically acceptable excipient, carrier, or vehicle.

In another aspect, the invention encompasses a method for treating or preventing hepatitis C virus infection in a patient in need thereof, comprising administering to the patient a therapeutically or prophylactically effective amount of a compound of the invention and an additional therapeutic agent, preferably an additional antiviral agent or an immunomodulatory agent.

DETAILED DESCRIPTION OF THE INVENTION

Where the following terms are used in this specification, they are used as defined below:

The terms "comprising," "having" and "including" are used herein in their open, non-limiting sense.

The term "alkyl", as used herein, unless otherwise indicated, includes $C_1$-$C_{12}$ saturated monovalent hydrocarbon radicals having straight, branched, or cyclic moieties (including fused and bridged bicyclic and spirocyclic moieties), or a combination of the foregoing moieties. For an alkyl group to have cyclic moieties, the group must have at least three carbon atoms.

The term "Me" means methyl, "Et" means ethyl, and "Ac" means acetyl.

The term "aryl", as used herein, unless otherwise indicated, includes an organic radical derived from an aromatic hydrocarbon by removal of one hydrogen, such as phenyl or naphthyl, containing a total of from 6 to 10 carbon atoms.

Unless defined otherwise "alkyl" or "aryl" are each optionally and independently substituted by 1-3 substituents selected from amino, cyano, halo, hydroxy, nitro, $C_1$-$C_6$ alkylamine, $C_1$-$C_6$ dialkylamine, $C_1$-$C_6$ alkyl, $C_1$-$C_6$ alkoxy, $C_1$-$C_6$ alkenyl, and $C_1$-$C_6$ hydroxyalkyl, wherein each alkyl is optionally substituted by one or more halo substituents, e.g., $CF_3$.

The term "immunomodulator" refers to natural or synthetic products capable of modifying the normal or aberrant immune system through stimulation or suppression.

The term "preventing" refers to the ability of a compound or composition of the invention to prevent a disease identified herein in patients diagnosed as having the disease or who are at risk of developing such disease. The term also encompasses preventing further progression of the disease in patients who are already suffering from or have symptoms of such disease.

The term "patient" or "subject" means an animal (e.g., cow, horse, sheep, pig, chicken, turkey, quail, cat, dog, mouse, rat, rabbit, guinea pig, etc.) or a mammal, including chimeric and transgenic animals and mammals. In the treatment or prevention of HCV infection, the term "patient" or "subject" preferably means a monkey or a human, most preferably a human. In a specific embodiment the patient or subject is infected by or exposed to the hepatitis C virus. In certain embodiments, the patient is a human infant (age 0-2), child (age 2-17), adolescent (age 12-17), adult (age 18 and up) or geriatric (age 70 and up) patient. In addition, the patient includes immunocompromised patients such as HIV positive patients, cancer patients, patients undergoing immunotherapy or chemotherapy. In a particular embodiment, the patient is a healthy individual, i.e., not displaying symptoms of other viral infections.

The term a "therapeutically effective amount" refers to an amount of the compound of the invention sufficient to provide a benefit in the treatment or prevention of viral disease, to delay or minimize symptoms associated with viral infection or viral-induced disease, or to cure or ameliorate the disease or infection or cause thereof. In particular, a therapeutically effective amount means an amount sufficient to provide a therapeutic benefit in vivo. Used in connection with an amount of a compound of the invention, the term preferably encompasses a non-toxic amount that improves overall therapy, reduces or avoids symptoms or causes of disease, or enhances the therapeutic efficacy of or synergies with another therapeutic agent.

The term a "prophylactically effective amount" refers to an amount of a compound of the invention or other active ingredient sufficient to result in the prevention of infection, recurrence or spread of viral infection. A prophylactically effective amount may refer to an amount sufficient to prevent initial infection or the recurrence or spread of the infection or a disease associated with the infection. Used in connection with an amount of a compound of the invention, the term preferably encompasses a non-toxic amount that improves overall prophylaxis or enhances the prophylactic efficacy of or synergies with another prophylactic or therapeutic agent.

The term "in combination" refers to the use of more than one prophylactic and/or therapeutic agents simultaneously or sequentially and in a manner that their respective effects are additive or synergistic.

The term "treating" refers to:

(i) preventing a disease, disorder, or condition from occurring in an animal that may be predisposed to the disease, disorder and/or condition, but has not yet been diagnosed as having it;

(ii) inhibiting the disease, disorder, or condition, i.e., arresting its development; and (iii) relieving the disease, disorder, or condition, i.e., causing regression of the disease, disorder, and/or condition.

The terms "R" and "S" indicate the specific stereochemical configuration of a substituent at an asymmetric carbon atom in a chemical structure as drawn.

The term "rac" indicates that a compound is a racemate, which is defined as an equimolar mixture of a pair of enantiomers. A "rac" compound does not exhibit optical activity. The chemical name or formula of a racemate is distinguished from those of the enantiomers by the prefix (±)- or rac- (or racem-) or by the symbols RS and SR.

The terms "endo" and "exo" are descriptors of the relative orientation of substituents attached to non-bridgehead atoms in a bicyclo[x.y.z]alkane (x≧y>z>0).

The terms "syn" and "anti" are descriptors of the relative orientation of substituents attached to bridgehead atoms in a bicyclo[x.y.z]alkane (x≧y>z>0).

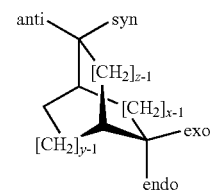

The term "exo" is given to a substituent (e.g., Br attached to C-2 in the example below) that is orientated towards the highest numbered bridge (z bridge, e.g., C-7 in example below); if the substituent is orientated away from the highest numbered bridge it is given the description "endo".

The term "syn" is given to a substituent attached to the highest numbered bridge (z bridge, e.g., F attached to C-7 in the example below) and is orientated towards the lowest numbered bridge (x bridge, e.g., C-2 and C-3 in example below); if the substiuent is orientated away from the lowest numbered bridge it is given the description "anti."

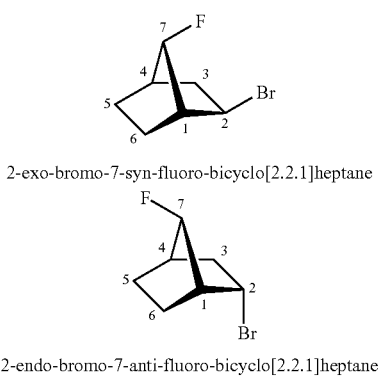

2-exo-bromo-7-syn-fluoro-bicyclo[2.2.1]heptane 2-endo-bromo-7-anti-fluoro-bicyclo[2.2.1]heptane The terms "cis" and "trans" are descriptors which show the relationship between two ligands attached to separate atoms that are connected by a double bond or are contained in a ring. The two ligands are said to be located cis to each other if they lie on the same side of a plane. If they are on opposite sides, their relative position is described as trans. The appropriate reference plane of a double bond is perpendicular to that of the relevant σ-bonds and passes through the double bond. For a ring it is the mean plane of the ring(s).

The compounds of the invention may exhibit the phenomenon of tautomerism. While a single drawing of a compound of the invention cannot expressly depict all possible tautomeric forms, it is to be understood that a compound of the invention is intended to represent any tautomeric form of the depicted compound and is not to be limited merely to a specific compound form depicted by the formula drawings. For illustration, and in no way limiting the range of tautomers, the compounds of the invention may exist as the following:

one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% free of other enantiomers or diastereomers of the compounds, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, compounds of the invention are intended to cover solvated as well as unsolvated forms of the identified structures. For example, the invention includes compounds of the indicated structure in both hydrated and non-hydrated forms. Other examples of solvates include the structures in combination with isopropanol, ethanol, methanol, DMSO, ethyl acetate, pentyl acetate, acetic acid, or ethanolamine.

In addition to compounds of the invention, the invention includes pharmaceutically acceptable prodrugs, pharmaceutically active metabolites, and pharmaceutically acceptable salts of such compounds and metabolites.

"A pharmaceutically acceptable prodrug" is a compound that may be converted under physiological conditions or by solvolysis to the specified compound or to a pharmaceutically acceptable salt of such compound prior to exhibiting its pharmacological effect(s). Typically, the prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the compounds of the invention using methods known in the art, such as those

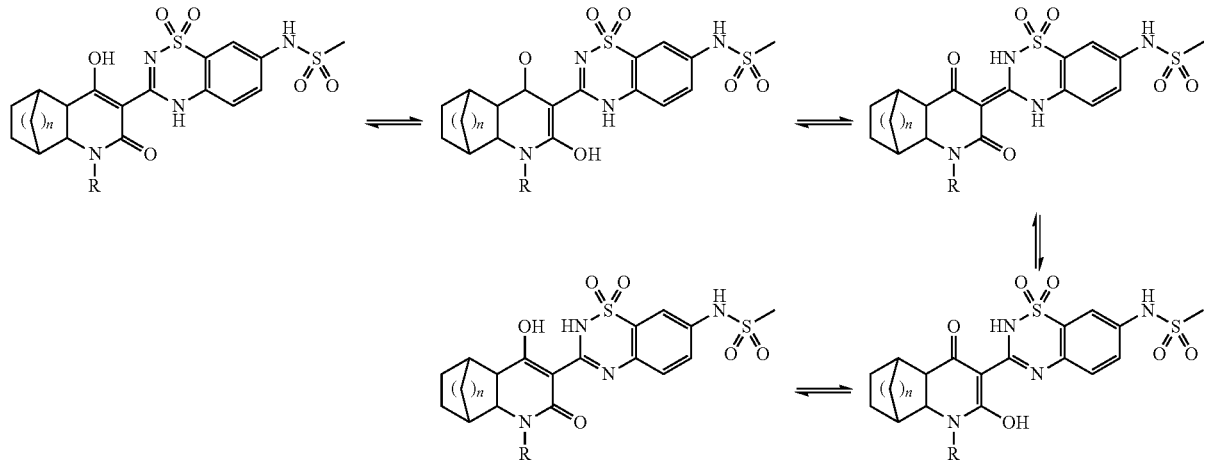

n = 1,2
R = $C_1$-$C_6$alkyl or (Aryl)$CH_2$—

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of described by *Burger's Medicinal Chemistry and Drug Chemistry*, 1, 172-178, 949-982 (1995). See also Bertolini et al., *J. Med. Chem.*, 40, 2011-2016 (1997); Shan, et al., *J. Pharm. Sci.*, 86 (7), 765-767; Bagshawe, *Drug Dev. Res.*, 34, 220-230 (1995); Bodor, *Advances in Drug Res.*, 13, 224-331 (1984); Bundgaard, *Design of Prodrugs* (Elsevier Press 1985); Larsen, *Design and Application of Prodrugs*, Drug Design and Development (Krogsgaard-Larsen et al., eds., Harwood Academic Publishers, 1991); Dear et al., *J. Chromatogr. B*, 748, 281-293 (2000); Spraul et al., *J. Pharmaceutical &*

*Biomedical Analysis,* 10, 601-605 (1992); and Prox et al., *Xenobiol.,* 3, 103-112 (1992).

"A pharmaceutically active metabolite" is intended to mean a pharmacologically active product produced through metabolism in the body of a specified compound or salt thereof. After entry into the body, most drugs are substrates for chemical reactions that may change their physical properties and biologic effects. These metabolic conversions, which usually affect the polarity of the compounds of the invention, alter the way in which drugs are distributed in and excreted from the body. However, in some cases, metabolism of a drug is required for therapeutic effect. For example, anticancer drugs of the anti-metabolite class must be converted to their active forms after they have been transported into a cancer cell.

Since most drugs undergo metabolic transformation of some kind, the biochemical reactions that play a role in drug metabolism may be numerous and diverse. The main site of drug metabolism is the liver, although other tissues may also participate.

A feature characteristic of many of these transformations is that the metabolic products, or "metabolites," are more polar than the parent drugs, although a polar drug does sometime yield a less polar product. Substances with high lipid/water partition coefficients, which pass easily across membranes, also diffuse back readily from tubular urine through the renal tubular cells into the plasma. Thus, such substances tend to have a low renal clearance and a long persistence in the body. If a drug is metabolized to a more polar compound, one with a lower partition coefficient, its tubular reabsorption will be greatly reduced. Moreover, the specific secretory mechanisms for anions and cations in the proximal renal tubules and in the parenchymal liver cells operate upon highly polar substances.

As a specific example, phenacetin (acetophenetidin) and acetanilide are both mild analgesic and antipyretic agents, but are transformed within the body to a more polar and more effective metabolite, p-hydroxyacetanilid (acetaminophen), which is widely used today. When a dose of acetanilide is given to a person, the successive metabolites peak and decay in the plasma sequentially. During the first hour, acetanilide is the principal plasma component. In the second hour, as the acetanilide level falls, the metabolite acetaminophen concentration reaches a peak. Finally, after a few hours, the principal plasma component is a further metabolite that is inert and can be excreted from the body. Thus, the plasma concentrations of one or more metabolites, as well as the drug itself, can be pharmacologically important.

"A pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an α-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal, co-crystal, or polymorphic forms, all of which are intended to be within the scope of the present invention and specified formulas.

Methods of Treatment and Prevention of Hepatitis C Viral Infections

The present invention provides methods for treating or preventing a hepatitis C virus infection in a patient in need thereof.

The present invention further provides methods for introducing a therapeutically effective amount of the compound of the invention or combination of such compounds into the blood stream of a patient in the treatment and/or prevention of hepatitis C viral infections.

The magnitude of a prophylactic or therapeutic dose of a compound of the invention or a pharmaceutically acceptable salt, solvate, or hydrate, thereof in the acute or chronic treatment or prevention of an infection will vary, however, with the nature and severity of the infection, and the route by which the active ingredient is administered. The dose, and in some cases the dose frequency, will also vary according to the infection to be treated, the age, body weight, and response of the individual patient. Suitable dosing regimens can be readily selected by those skilled in the art with due consideration of such factors.

The methods of the present invention are particularly well suited for human patients. In particular, the methods and doses of the present invention can be useful for immunocompromised patients including, but not limited to cancer patients, HIV infected patients, and patients with an immunodegenerative disease. Furthermore, the methods can be useful for immunocompromised patients currently in a state of remission. The methods and doses of the present invention are also useful for patients undergoing other antiviral treatments. The prevention methods of the present invention are particularly useful for patients at risk of viral infection. These patients include, but are not limited to health care workers, e.g., doctors, nurses, hospice care givers; military personnel; teachers; childcare workers; patients traveling to, or living in, foreign locales, in particular third world locales including social aid workers, missionaries, and foreign diplomats. Finally, the methods and compositions include the treatment of refractory patients or patients resistant to treatment such as resistance to reverse transcriptase inhibitors, protease inhibitors, etc.

Doses

Toxicity and efficacy of the compounds of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from the cell culture assays and animal studies can be used in formulating a range of dosage of the compounds for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture; alternatively, the dose of the compound of the invention may be formulated in animal models to achieve a circulating plasma concentration range of the compound that corresponds to the concentration required to achieve a fixed magnitude of response. Such information can be used to more accurately determine useful doses in humans. Levels in plasma may be measured, for example, by high performance liquid chromatography.

The protocols and compositions of the invention are preferably tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which cells that are responsive to the effects of the compounds of the invention are exposed to the ligand and the magnitude of response is measured by an appropriate technique. The assessment of the compound of the invention is then evaluated with respect to the potency of the compound of the invention, and the degree of conversion of the compound of the invention prodrug. Compounds for use in methods of the invention can be tested in suitable animal model systems prior to testing in humans, including but not limited to in rats, mice, chicken, cows, monkeys, rabbits, hamsters, etc. The compounds can then be used in the appropriate clinical trials.

The magnitude of a prophylactic or therapeutic dose of a prodrug of a compound of the invention or a pharmaceutically acceptable salt, solvate, or hydrate thereof in the acute or chronic treatment or prevention of an infection or condition will vary with the nature and severity of the infection, and the route by which the active ingredient is administered. The dose, and perhaps the dose frequency, will also vary according to the infection to be treated, the age, body weight, and response of the individual patient. Suitable dosing regimens can be readily selected by those skilled in the art with due consideration of such factors. In one embodiment, the dose administered depends upon the specific compound to be used, and the weight and condition of the patient. Also, the dose may differ for various particular compounds of the invention; suitable doses can be predicted on the basis of the aforementioned in vitro measurements and on the basis of animal studies, such that smaller doses will be suitable for those compounds of the invention that show effectiveness at lower concentrations than other compounds of the invention when measured in the systems described or referenced herein. In general, the dose per day is in the range of from about 0.001 to 100 mg/kg, preferably about 1 to 25 mg/kg, more preferably about 5 to 15 mg/kg. For treatment of humans infected by hepatitis C viruses, about 0.1 mg to about 15 g per day is administered in about one to four divisions a day, preferably 100 mg to 12 g per day, more preferably from 100 mg to 8000 mg per day.

Additionally, the recommended daily dose ran can be administered in cycles as single agents or in combination with other therapeutic agents. In one embodiment, the daily dose is administered in a single dose or in equally divided doses. In a related embodiment, the recommended daily dose can be administered once time per week, two times per week, three times per week, four times per week or five times per week.

In one embodiment, the compounds of the invention are administered to provide systemic distribution of the compound within the patient. In a related embodiment, the compounds of the invention are administered to produce a systemic effect in the body.

In another embodiment the compounds of the invention are administered via oral, mucosal (including sublingual, buccal, rectal, nasal, or vaginal), parenteral (including subcutaneous, intramuscular, bolus injection, intraarterial, or intravenous), transdermal, or topical administration. In a specific embodiment the compounds of the invention are administered via mucosal (including sublingual, buccal, rectal, nasal, or vaginal), parenteral (including subcutaneous, intramuscular, bolus injection, intraarterial, or intravenous), transdermal, or topical administration. In a further specific embodiment, the compounds of the invention are administered via oral administration. In a further specific embodiment, the compounds of the invention are not administered via oral administration.

Different therapeutically effective amounts may be applicable for different infections, as will be readily known by those of ordinary skill in the art. Similarly, amounts sufficient to treat or prevent such infections, but insufficient to cause, or sufficient to reduce, adverse effects associated with conventional therapies are also encompassed by the above described dosage amounts and dose frequency schedules.

Combination Therapy

Specific methods of the invention further comprise the administration of an additional therapeutic agent (i.e., a therapeutic agent other than a compound of the invention). In certain embodiments of the present invention, the compounds of the invention can be used in combination with at least one other therapeutic agent. Therapeutic agents include, but are not limited to antibiotics, antiemetic agents, antidepressants, and antifungal agents, anti-inflammatory agents, antiviral agents, anticancer agents, immunomodulatory agents, α-interferons, β-interferons, ribavirin, alkylating agents, hormones, cytokines, or toll receptor-like modulators. In one embodiment the invention encompasses the administration of an additional therapeutic agent that is HCV specific or demonstrates anti-HCV activity.

The compounds of the invention can be administered or formulated in combination with antibiotics. For example, they can be formulated with a macrolide (e.g., tobramycin (Tobi®)), a cephalosporin (e.g., cephalexin (Keflex), cephradine (Velosef), cefuroxime (Ceftin®), cefprozil (Cefzil®), cefaclor (Ceclor®), cefixime (Suprax®) or cefadroxil (Duricef®)), a clarithromycin (e.g., clarithromycin (Biaxin®)), an erythromycin (e.g., erythromycin (EMycin®)), a penicillin (e.g., penicillin V (V-Cillin K® or Pen Vee K®)) or a quinolone (e.g., ofloxacin (Floxin®), ciprofloxacin (Cipro®) or norfloxacin (Noroxin®)), aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitro furans (e.g., furaltadone, and furazolium chloride), quinolones and analogs thereof (e.g., cinoxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

The compounds of the invention can also be administered or formulated in combination with an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, tropisetron, and mixtures thereof.

The compounds of the invention can be administered or formulated in combination with an antidepressant. Suitable antidepressants include, but are not limited to, binedaline, caroxazone, citalopram, dimethazan, fencamine, indalpine, indeloxazine hydrochloride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

The compounds of the invention can be administered or formulated in combination with an antifungal agent. Suitable antifungal agents include but are not limited to amphotericin B, itraconazole, ketoconazole, fluconazole, intrathecal, flucytosine, miconazole, butoconazole, clotrimazole, nystatin, terconazole, tioconazole, ciclopirox, econazole, haloprogrin, naftifine, terbinafine, undecylenate, and griseofulvin.

The compounds of the invention can be administered or formulated in combination with an anti-inflammatory agent. Useful anti-inflammatory agents include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofin; steroids including, but not limited to, alclometasone diproprionate, amcinonide, beclomethasone dipropionate, betametasone, betamethasone benzoate, betamethasone diproprionate, betamethasone sodium phosphate, betamethasone valerate, clobetasol proprionate, clocortolone pivalate, hydrocortisone, hydrocortisone derivatives, desonide, desoximatasone, dexamethasone, flunisolide, flucoxinolide, flurandrenolide, halcinocide, medrysone, methylprednisolone, methprednisolone acetate, methylprednisolone sodium succinate, mometasone furoate, paramethasone acetate, prednisolone, prednisolone acetate, prednisolone sodium phosphate, prednisolone tebuatate, prednisone, triamcinolone, triamcinolone acetonide, triamcinolone diacetate, and triamcinolone hexacetonide; and other anti-inflammatory agents including, but not limited to, methotrexate, colchicine, allopurinol, probenecid, sulfinpyrazone and benzbromarone.

The compounds of the invention can be administered or formulated in combination with another antiviral agent. Useful antiviral agents include, but are not limited to, protease inhibitors, nucleoside reverse transcriptase inhibitors, non-nucleoside reverse transcriptase inhibitors and nucleoside analogs. The antiviral agents include but are not limited to zidovudine, acyclovir, gangcyclovir, vidarabine, idoxuridine, trifluridine, levovirin, viramidine, ribavirin, and taribavirin, as well as foscarnet, amantadine, rimantadine, saquinavir, indinavir, amprenavir, lopinavir, ritonavir, the α-interferons, β-interferons, adefovir, clevadine, entecavir, pleconaril, BMS-824393, and GI-5005.

The compound of the invention can be administered or formulated in combination with an immunomodulatory agent. Immunomodulatory agents include, but are not limited to, methothrexate, leflunomide, cyclophosphamide, cyclosporine A, mycophenolate mofetil, rapamycin (sirolimus), mizoribine, deoxyspergualin, brequinar, malononitriloamindes (e.g., leflunamide), T cell receptor modulators, and cytokine receptor modulators, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. Examples of T cell receptor modulators include, but are not limited to, anti-T cell receptor antibodies (e.g., anti-CD4 antibodies (e.g., cM-T412 (Boehringer), IDEC-CE9.1® (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies, anti-CD11a antibodies (e.g., Xanelim (Genentech)), anti-B7 antibodies (e.g., IDEC-114 (IDEC)), CTLA4-immunoglobulin, and toll receptor-like (TLR) modulators (e.g., ANA773, IMO-2125, PF-04878691). Examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-α, interferon (IFN)-α, IFN-β, IFN-γ, and GM-CSF), anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-α antibodies, anti-IL-1β antibodies, anti-IL-6 antibodies, anti-IL-8 antibodies (e.g., ABX-IL-8 (Abgenix)), and anti-IL-12 antibodies).

The compounds of the invention can be administered or formulated in combination with an agent which inhibits viral enzymes, including but not limited to inhibitors of HCV protease, such as VX-500, VBY-376, BMS-650032, MK-7009, TMC-435350, BI-201335, SCH-503034 (boceprevir), ITMN-191, VX-950 (telaprevir), SCH900518 (narlaprevir), VX-813, VX-985, PHX1766, ABT-450, ACH-1625, ACH-1095, IDX136, IDX316, and ITMN-5489; inhibitors of NS5B polymerase such as GS-9190, MK-3281, VCH-759 (VX-759), VCH-916, ABT-333, BMS-791325, PF-00868554, IDX-184, R7128, PSI-6130, R1626, PSI-7851, VCH-222 (VX-222), ABT-072, and BI207127; and inhibitors of the NS5A protein, such as BMS-790052, A-831, and AZD2836.

The compounds of the invention can be administered or formulated in combination with an agent which inhibits HCV polymerase such as those described in Wu, *Curr Drug Targets Infect Disord.* 2003, 3(3), 207-19 or in combination with compounds that inhibit the helicase function of the virus such as those described in Bretner M, et al. *Nucleosides Nucleotides Nucleic Acids.* 2003, 22(5-8), 1531, or with inhibitors of other HCV specific targets such as those described in Zhang X., *IDrugs* 2002, 5(2), 154-8.

The compounds of the invention can be administered or formulated in combination with an agent which inhibits viral replication.

The compounds of the invention can be administered or formulated in combination with an agent which inhibits cyclophilins. Examples of cyclophilin inhibitors include, but are not limited to, Debio-025, NIM-811, and SCY-635.

The compounds of the invention can be administered or formulated in combination with cytokines. Examples of cytokines include, but are not limited to, interleukin-2 (IL-2), interleukin-3 (IL-3), interleukin-4 (IL-4), interleukin-5 (IL-5), interleukin-6 (IL-6), interleukin-7 (IL-7), interleukin-9 (IL-9), interleukin-10 (IL-10), interleukin-12 (IL-12), interleukin 15 (IL-15), interleukin 18 (IL-18), platelet derived growth factor (PDGF), erythropoietin (Epo), epidermal growth factor (EGF), fibroblast growth factor (FGF), granulocyte macrophage stimulating factor (GM-CSF), granulocyte colony stimulating factor (G-CSF), macrophage colony stimulating factor (M-CSF), prolactin, and interferon (IFN), e.g., IFN-α, and IFN-γ).

The compounds of the invention can be administered or formulated in combination with hormones. Examples of hormones include, but are not limited to, luteinizing hormone releasing hormone (LHRH), growth hormone (GH), growth hormone releasing hormone, ACTH, somatostatin, somatotropin, somatomedin, parathyroid hormone, hypothalamic releasing factors, insulin, glucagon, enkephalins, vasopressin, calcitonin, heparin, low molecular weight heparins, heparinoids, synthetic and natural opioids, insulin thyroid stimulating hormones, and endorphins The compounds of the invention can be administered or formulated in combination with β-interferons which include, but are not limited to, interferon β-1a, interferon β-1b.

The compounds of the invention can be administered or formulated in combination with α-interferons which include, but are not limited to, interferon α-1, interferon α-2a (roferon), interferon α-2b, intron, Peg-Intron, Pegasys, consensus interferon (infergen) and albuferon. The compounds of the invention can also be administered or formulated in combination with interferons such as BLX-883 (Locteron), Omega interferon, and PEG-Interferon lambda.

The compounds of the invention can be administered or formulated in combination with an absorption enhancer, particularly those which target the lymphatic system, including, but not limited to sodium glycocholate; sodium caprate; N-lauryl-β-D-maltopyranoside; EDTA; mixed micelle; and those reported in Muranishi *Crit. Rev. Ther. Drug Carrier Syst.*, 7, 1-33, which is hereby incorporated by reference in its entirety. Other known absorption enhancers can also be used. Thus, the invention also encompasses a pharmaceutical composition comprising one or more compounds of the invention and one or more absorption enhancers.

The compounds of the invention can be administered or formulated in combination with a cytochrome P450 monooxygenase inhibitor, such as, but not limited to, ritonavir or a pharmaceutically acceptable salt, ester, and prodrug thereof to improve the pharmacokinetics (e.g., increased half-life, increased time to peak plasma concentration, increased blood levels) of a compound of the invention that is metabolized by cytochrome P450 monooxygenase. Thus, the invention also encompasses a pharmaceutical composition comprising compounds of the invention and one or more cytochrome P450 monooxygenase inhibitors.

The compounds of the invention can be administered in combination with food to enhance absorption of the compounds of the invention in the gastrointestinal tract and to increase the bioavailability of the compounds of the invention.

The compounds of the invention can be administered or formulated in combination with an alkylating agent. Examples of alkylating agents include, but are not limited to nitrogen mustards, ethylenimines, methylmelamines, alkyl sulfonates, nitrosoureas, triazenes, mechlorethamine, cyclophosphamide, ifosfamide, melphalan, chlorambucil, hexamethylmelaine, thiotepa, busulfan, carmustine, streptozocin, dacarbazine and temozolomide.

The compounds of the invention and the other therapeutics agent can act additively or, more preferably, synergistically. In one embodiment, a composition comprising a compound of the invention is administered concurrently with the administration of another therapeutic agent, which can be part of the same composition or in a different composition from that comprising the compounds of the invention. In another embodiment, a compound of the invention is administered prior to or subsequent to administration of another therapeutic agent. In a separate embodiment, a compound of the invention is administered to a patient who has not previously undergone or is not currently undergoing treatment with another therapeutic agent, particularly an antiviral agent.

In one embodiment, the methods of the invention comprise the administration of one or more compounds of the invention without an additional therapeutic agent.

Pharmaceutical Compositions and Dosage Forms

Pharmaceutical compositions and single unit dosage forms comprising a compound of the invention, or a pharmaceutically acceptable salt, or hydrate thereof, are also encompassed by the invention. Individual dosage forms of the invention may be suitable for oral, mucosal (including sublingual, buccal, rectal, nasal, or vaginal), parenteral (including subcutaneous, intramuscular, bolus injection, intraarterial, or intravenous), transdermal, or topical administration. Pharmaceutical compositions and dosage forms of the invention typically also comprise one or more pharmaceutically acceptable excipients. Sterile dosage forms are also contemplated.

In an alternative embodiment, pharmaceutical composition encompassed by this embodiment includes a compound of the invention, or a pharmaceutically acceptable salt, or hydrate thereof, and at least one additional therapeutic agent. Examples of additional therapeutic agents include, but are not limited to, those listed above.

The composition, shape, and type of dosage forms of the invention will typically vary depending on their use. For example, a dosage form used in the acute treatment of a disease or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990). Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise compounds of the invention, or a pharmaceutically acceptable salt or hydrate thereof comprise 0.1 mg to 1500 mg per unit to provide doses of about 0.01 to 200 mg/kg per day.

Oral Dosage Forms

Pharmaceutical compositions of the invention that are suitable for oral administration can be presented as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients of the invention can be administered by controlled release means or by delivery devices that are well known to those of ordinary skill in the art. Examples include, but are not limited to, those described in U.S. Pat. Nos. 3,845, 770; 3,916,899; 3,536,809; 3,598,123; and 4,008,719, 5,674, 533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry and/or lyophilized products ready to be dissolved or suspended in a pharmaceutically acceptable vehicle for injection (reconstitutable powders), suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal Dosage Forms

Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Topical Dosage Forms

Topical dosage forms of the invention include, but are not limited to, creams, lotions, ointments, gels, solutions, emulsions, suspensions, or other forms known to one of skill in the art. See, e.g., *Remington's Pharmaceutical Sciences*, 18th eds., Mack Publishing, Easton Pa. (1990); and *Introduction to Pharmaceutical Dosage Forms*, 4th ed., Lea & Febiger, Philadelphia (1985).

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

Mucosal Dosage Forms

Mucosal dosage forms of the invention include, but are not limited to, ophthalmic solutions, sprays and aerosols, or other forms known to one of skill in the art. See, e.g., *Remington's Pharmaceutical Sciences*, 18th eds., Mack Publishing, Easton Pa. (1990); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels. In one embodiment, the aerosol comprises a carrier. In another embodiment, the aerosol is carrier free.

The compounds of the invention may also be administered directly to the lung by inhalation. For administration by inhalation, a compound of the invention can be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas can be used to deliver a compound of the invention directly to the lung. MDI devices are available from a number of suppliers such as 3M Corporation, Aventis, Boehringer Ingelheim, Forest Laboratories, Glaxo-Wellcome, Schering Plough and Vectura.

Alternatively, a Dry Powder Inhaler (DPI) device can be used to administer a compound of the invention to the lung (see, e.g., Raleigh et al., *Proc. Amer. Assoc. Cancer Research Annual Meeting*, 1999, 40, 397, which is herein incorporated by reference). DPI devices typically use a mechanism such as a burst of gas to create a cloud of dry powder inside a container, which can then be inhaled by the patient. DPI devices are also well known in the art and can be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator can be formulated containing a powder mix of the compound and a suitable powder base such as lactose or starch for these systems.

Another type of device that can be used to deliver a compound of the invention to the lung is a liquid spray device supplied, for example, by Aradigm Corporation. Liquid spray systems use extremely small nozzle holes to aerosolize liquid drug formulations that can then be directly inhaled into the lung.

In one embodiment, a nebulizer device is used to deliver a compound of the invention to the lung. Nebulizers create aerosols from liquid drug formulations by using, for example, ultrasonic energy to form fine particles that can be readily inhaled (See e.g., Verschoyle et al., *British J. Cancer*, 1999, 80, Suppl 2, 96, which is herein incorporated by reference). Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et al., U.S. Pat. No. 5,970,974, which are herein incorporated by reference), Aventis and Batelle Pulmonary Therapeutics.

In one embodiment, an electrohydrodynamic ("EHD") aerosol device is used to deliver compounds of the invention to the lung. EHD aerosol devices use electrical energy to aerosolize liquid drug solutions or suspensions (see, e.g., Noakes et al., U.S. Pat. No. 4,765,539; Coffee, U.S. Pat. No. 4,962,885; Coffee, PCT Application, WO 94/12285; Coffee, PCT Application, WO 94/14543; Coffee, PCT Application, WO 95/26234, Coffee, PCT Application, WO 95/26235, Coffee, PCT Application, WO 95/32807, which are herein incorporated by reference). The electrochemical properties of the compounds of the invention formulation may be important parameters to optimize when delivering this drug to the lung with an EHD aerosol device and such optimization is routinely performed by one of skill in the art. EHD aerosol devices may more efficiently delivery drugs to the lung than existing pulmonary delivery technologies. Other methods of intra-pulmonary delivery of compounds of the invention will be known to the skilled artisan and are within the scope of the invention.

Liquid drug formulations suitable for use with nebulizers and liquid spray devices and EHD aerosol devices will typically include a compound of the invention with a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of the compound of the invention. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611, which are herein incorporated by reference) A compound of the invention can also be formulated in rectal or vaginal compositions such as suppositories or retention enemas, e.g., containing conventional suppository bases such as cocoa butter or other glycerides.

In addition to the formulations described previously, a compound of the invention can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Alternatively, other pharmaceutical delivery systems can be employed. Liposomes, emulsions, self-emulsifying (SEDDS), and self micro-emulsifying systems (SMEDDS) are well known examples of delivery vehicles that can be used to deliver compositions of the invention. Such systems can also contain fatty acids, bile salts and mixtures of mono-, di- and triglycerides to ameliorate potential food effects. Other functional lipid excipients include esters of glycerol, PEG-esters, propylene glycol esters and polyglycerol esters. Certain organic solvents such as dimethylsulfoxide can also be employed, although usually at the cost of greater toxicity. A compound of the invention can also be delivered in a controlled release system. In one embodiment, a pump can be used (Sefton, *CRC Crit. Ref Biomed Eng.*, 1987, 14, 201; Buchwald et al., *Surgery*, 1980, 88, 507; Saudek et al., *N. Engl. J. Med.*, 1989, 321, 574). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, *J. Macromol. Sci. Rev. Macromol. Chem.*, 1983, 23, 61; see also Levy et al., *Science*, 1985, 228, 190; During et al., *Ann. Neurol.*, 1989, 25, 351; Howard et al., *J. Neurosurg.*, 71, 105 (1989). In yet another embodiment, a controlled-release system can be placed in proximity of the target of the compounds of the invention, e.g., the lung, thus requiring only a fraction of the systemic dose (see, e.g., Goodson, in *Medical Applications of Controlled Release*, supra, vol. 2, pp. 115 (1984)). Other controlled-release system can be used (see, e.g., Langer, *Science*, 1990, 249, 1527).

Suitable excipients (e.g., carriers and diluents) and other materials that can be used to provide mucosal dosage forms encompassed by this invention are well known to those skilled in the pharmaceutical arts, and depend on the particular site or method which a given pharmaceutical composition or dosage form will be administered. With that fact in mind, typical excipients include, but are not limited to, water, ethanol, ethylene glycol, propylene glycol, butane-1,3-diol, isopropyl myristate, isopropyl palmitate, mineral oil, and mixtures thereof, which are non-toxic and pharmaceutically acceptable. Examples of such additional ingredients are well known in the art. See, e.g., Remington's Pharmaceutical Sciences, 18th eds., Mack Publishing, Easton Pa. (1990).

The pH of a pharmaceutical composition or dosage form, or of the tissue to which the pharmaceutical composition or dosage form is applied, can also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Kits

The invention provides a pharmaceutical pack or kit comprising one or more containers comprising a compound of the invention useful for the treatment or prevention of a Hepatitis C virus infection. In other embodiments, the invention provides a pharmaceutical pack or kit comprising one or more containers comprising a compound of the invention useful for the treatment or prevention of a Hepatitis C virus infection and one or more containers comprising an additional therapeutic agent, including but not limited to those listed above, in particular an antiviral agent, an interferon, an agent which inhibits viral enzymes, or an agent which inhibits viral replication, preferably the additional therapeutic agent is HCV specific or demonstrates anti-HCV activity.

The invention also provides a pharmaceutical pack or kit comprising one or more containers comprising one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The inventive agents may be prepared using the reaction routes and synthesis schemes as described below, employing the general techniques known in the art using starting materials that are readily available. The synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or generally known in the art will be recognized as having applicability for preparing other compounds of the invention.

Preparation of Compounds

In the synthetic schemes described below, unless otherwise indicated all temperatures are set forth in degrees Celsius and all parts and percentages are by weight.

Reagents were purchased from commercial suppliers such as Aldrich Chemical Company or Lancaster Synthesis Ltd. and were used without further purification unless otherwise indicated. All solvents were purchased from commercial suppliers such as Aldrich, EMD Chemicals or Fisher and used as received.

The reactions set forth below were done generally under a positive pressure of argon or nitrogen at an ambient temperature (unless otherwise stated) in anhydrous solvents, and the reaction flasks were fitted with rubber septa for the introduction of substrates and reagents via syringe. Glassware was oven dried and/or heat dried.

The reactions were assayed by TLC and/or analyzed by LC-MS or HPLC and terminated as judged by the consumption of starting material. Analytical thin layer chromatography (TLC) was performed on glass-plates precoated with silica gel 60 $F_{254}$ 0.25 mm plates (EMD Chemicals), and visualized with UV light (254 nm) and/or iodine on silica gel and/or heating with TLC stains such as ethanolic phosphomolybdic acid, ninhydrin solution, potassium permanganate solution or ceric sulfate solution. Preparative thin layer chromatography (prepTLC) was performed on glass-plates precoated with silica gel 60 $F_{254}$ 0.5 mm plates (20×20 cm, from Thomson Instrument Company) and visualized with UV light (254 nm).

Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ and/or $MgSO_4$ prior to filtration and evaporation of the solvents under reduced pressure on a rotary evaporator and noted as solvents removed in vacuo. Column chromatography was completed under positive pressure using Merck silica gel 60, 230-400 mesh or 50-200 mesh neutral alumina, ISCO Flash-chromatography using prepacked RediSep silica gel columns, or Analogix flash column chromatography using prepacked SuperFlash silica gel columns. Hydrogenolysis was done at the pressure indicated in the examples or at ambient pressure.

$^1$H-NMR spectra and $^{13}$C-NMR were recorded on a Varian Mercury-VX400 instrument operating at 400 MHz. NMR spectra were obtained as $CDCl_3$ solutions (reported in ppm), using chloroform as the reference standard (7.27 ppm for the proton and 77.00 ppm for carbon), $CD_3OD$ (3.4 and 4.8 ppm for the protons and 49.3 ppm for carbon), DMSO-$d_6$ (2.49 ppm for proton), or internally tetramethylsilane (0.00 ppm) when appropriate. Other NMR solvents were used as needed. When peak multiplicities are reported, the following abbreviations are used: s (singlet), d (doublet), t (triplet), q (quartet), m (multiplet), br (broadened), bs (broad singlet), dd (doublet of doublets), dt (doublet of triplets). Coupling constants, when given, are reported in Hertz (Hz).

Infrared (IR) spectra were recorded on an ATR FT-IR Spectrometer as neat oils or solids, and when given are reported in wave numbers ($cm^{-1}$). Mass spectra reported are (+)-ES or APCI (+) LC/MS conducted by the Analytical Chemistry Department of Anadys Pharmaceuticals, Inc. Elemental analyses were conducted by the Atlantic Microlab, Inc. in Norcross, Ga. Melting points (mp) were determined on an open capillary apparatus, and are uncorrected.

The described synthetic pathways and experimental procedures utilize many common chemical abbreviations, 2,2-DMP (2,2-dimethoxypropane), Ac (acetyl), ACN (acetonitrile), Bn (benzyl), BnOH (benzyl alcohol), Boc (tert-butoxycarbonyl), $Boc_2O$ (di-tert-butyl dicarbonate), Bz (benzoyl), CSI (chlorosulfonyl isocyanate), DBU (1,8-diazabicyclo[5.4.0]undec-7-ene), DCC(N,N'-dicyclohexylcarbodiimide), DCE (1,2-dichloroethane), DCM (dichloromethane), DEAD (diethylazodicarboxylate), DIEA (diisopropylethylamine), DMA (N,N-dimethylacetamide), DMAP (4-(N,N-dimethylamino)pyridine), DMF (N,N-dimethylformamide), DMSO (dimethyl sulfoxide), EDC (1-(3-dimethylaminopropyl)-3-ethylcarbodiimide hydrochloride), Et (ethyl), EtOAc (ethyl acetate), EtOH (ethanol), HATU (O-(7-azabenzotriazol-1-yl)-1,1,3,3-tetramethyluronium hexafluorophosphate), HBTU (O-benzotriazol-1-yl-N,N,N', N'-tetramethyluronium hexafluorophosphate), HF (hydrogen fluoride), HOAc (acetic acid), HOBT (1-hydroxybenzotriazole hydrate), HPLC (high pressure liquid chromatography), IPA (isopropyl alcohol), KHMDS (potassium bis(trimethylsilyl)amide), $KN(TMS)_2$ (potassium bis(trimethylsilyl) amide), $KO^tBu$ (potassium tert-butoxide), LDA (lithium diisopropylamine), MCPBA (3-chloroperbenzoic acid), Me (methyl), MeCN (acetonitrile), MeOH (methanol), NaBH(OAc)$_3$ (sodium triacetoxyborohydride), NaCNBH$_3$ (sodium cyanoborohydride), NaH (sodium hydride), NaN(TMS)$_2$ (sodium bis(trimethylsilyl)amide), NaOAc (sodium acetate), NaOEt (sodium ethoxide), Phe (phenylalanine), PPTS (pyridinium p-toluenesulfonate), PS (polymer supported), Py (pyridine), pyBOP (benzotriazol-1-yloxy)tripyrrolidinophosphonium hexafluorophosphate), TEA (triethylamine), TFA (trifluoroacetic acid), TFAA (trifluoroacetic anhydride), THF (tetrahydrofuran), TLC (thin layer chromatography), Tol (toluoyl), Val (valine), and the like.

Scheme 1 provides a general procedure that was used to prepare saturated 5,6-dihydro-1H-pyridin-2-one compounds of the invention.

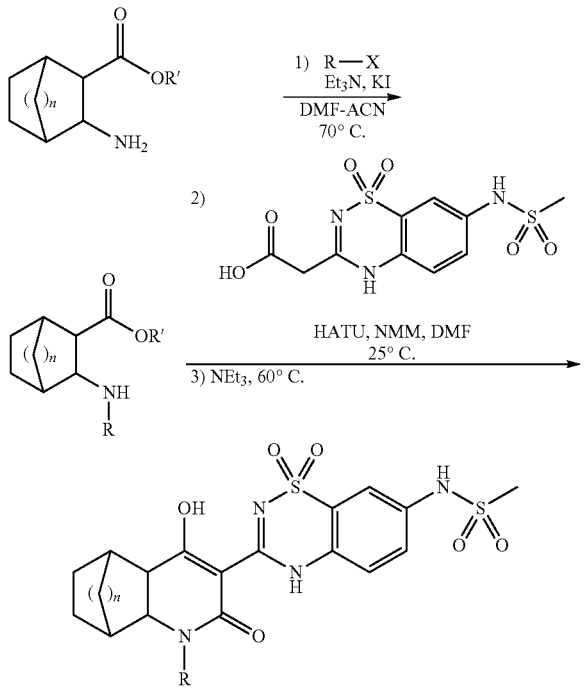

The saturated cyclic β-amino acid ester intermediates (or salts thereof, (e.g., hydrochlorides or CSA salts)), which can be obtained as described in U.S. patent application Ser. No. 12/061,499, can be treated with an alkylating agent (e.g., substituted benzyl halides or aliphatic halides) in the presence of a base, such as triethylamine, to afford the saturated cyclic N-substituted-β-amino acid ester intermediates shown. Coupling with (7-methanesulfonylamino-1,1-dioxo-1,4-dihydro-1$\lambda^6$-benzo[1,2,4]thiadiazin-3-yl)-acetic acid (prepared as described in U.S. Patent Application Publication No. US 2008/0031852) using standard peptide coupling conditions used for the formation of amide bonds, such as HATU, followed by cyclization in the presence of a base (e.g., triethylamine) gives the desired saturated 5,6-dihydro-1H-pyridin-2-one compounds.

General Experimental Procedure A:

A 0.2 M solution of the saturated cyclic β-amino acid ester salt (all hydrochloride salts except for the intermediate used in Example 1, where the (1S)-(+)-10-camphorsulfonic acid salt was employed) in N,N-dimethylformamide (1 mL, 0.2 mmol) was combined with a 2.0 M solution of an aliphatic or substituted benzylic bromide in N,N-dimethylformamide (0.1 mL, 0.2 mmol). Triethylamine (0.1 mL, 0.72 mmol) was added and the mixture was shaken at 70° C. for 16 h. Upon cooling to 25° C., a 0.4 M solution of 7-methanesulfonylamino-1,1-dioxo-1,4-dihydro-1$\lambda^6$-benzo[1,2,4]thiadiazin-3-yl)-acetic acid (prepared as described in Example 17 g of US Patent Application No. US 2008/0031852) in N,N-dimethylformamide (0.5 mL, 0.2 mmol) was added followed by a 0.4 M solution of O-(7-azabenzotriazol-1-yl)-1,1,3,3-tetramethyluronium hexafluorophosphate in N,N-dimethylformamide (0.5 mL, 0.2 mmol) followed by N-methylmorpholine (0.1 mL, 0.91 mmol). The mixture was shaken at 25° C. for 4 h. Triethylamine (0.1 mL, 0.72 mmol) was added and the mixture was shaken at 60° C. for 16 h. Upon cooling to 25° C., the mixture was concentrated in vacuo to a thick oil. The oil was partitioned between dichloromethane (3 mL) and 1.0 M aqueous hydrochloric acid solution (3 mL). The organic phase was loaded directly onto a prepacked RediSep silica gel column and purified by ISCO flash chromatography (0-100% ethyl acetate in hexanes, 15 min). The products were further purified by reverse phase HPLC (30-100% acetonitrile in water with 0.05% trifluoroacetic acid, 7 min, column: Phenomenex Luna 5μ C18 50×21.2 mm).

Scheme 2 provides an alternate general procedure that was used to prepare saturated 5,6-dihydro-1H-pyridin-2-one compounds of the invention.

Alternatively, the saturated cyclic β-amino acid ester intermediates (or salts thereof, (e.g., hydrochlorides or CSA salts), which can be obtained as described in U.S. patent application Ser. No. 12/061,499, can be treated with aldehydes (e.g., substituted benzaldehydes) in the presence of a reducing agent, such as sodium cyanoborohydride, to afford the saturated cyclic N-substituted-β-amino acid ester intermediates shown. Coupling with a (7-methanesulfonylamino-1,1-dioxo-1,4-dihydro-1$\lambda^6$-benzo[1,2,4]thiadiazin-3-yl)-acetic acid (prepared as described in U.S. Patent Application Publication No. US 2008/0031852) using standard peptide coupling conditions used for the formation of amide bonds, such as HATU, followed by cyclization in the presence of a base (e.g., triethylamine) gives the desired saturated 5,6-dihydro-1H-pyridin-2-one compounds.

General Experimental Procedure B:

Sodium acetate (0.033 g, 0.4 mmol) was added to a 0.1 M solution of the saturated cyclic β-amino acid ester hydrochloride salt. Upon dissolution, the substituted benzaldehyde (0.2 mmol) was added to the solution. The mixture was shaken for 15 min. at 25° C. Sodium cyanoborohydride (0.026 g, 0.4 mmol) was added and the mixture was shaken at 25° C. for 16 h. The mixture was concentrated in vacuo to a thick paste. The paste was partitioned between ethyl acetate (12 mL) and saturated aqueous sodium bicarbonate solution (12 mL). The organic phase was concentrated in vacuo to a thick oil.

The oil was dissolved in N,N-dimethylformamide (1 mL) and a 0.4 M solution of 7-methanesulfonylamino-1,1-dioxo-1,4-dihydro-1$\lambda^6$-benzo[1,2,4]thiadiazin-3-yl)-acetic acid (prepared as described in Example 17 g of US Patent Application No. US 2008/0031852) in N,N-dimethylformamide (0.5 mL, 0.2 mmol) was added followed by a 0.4 M solution of O-(7-azabenzotriazol-1-yl)-1,1,3,3-tetramethyluronium hexafluorophosphate in N,N-dimethylformamide (0.5 mL, 0.2 mmol) followed by N-methylmorpholine (0.1 mL, 0.91 mmol). The mixture was shaken at 25° C. for 4 h. Triethylamine (0.1 mL, 0.72 mmol) was added and the mixture was shaken at 60° C. for 16 h.

Upon cooling to 25° C., the mixture was concentrated in vacuo to a thick oil. The oil was partitioned between dichloromethane (3 mL) and 1.0 M aqueous hydrochloric acid solution (3 mL). The organic phase was loaded directly onto a prepacked RediSep silica gel column and purified by ISCO flash chromatography (0-100% ethyl acetate in hexanes, 15 min). The products were further purified by reverse phase HPLC (30-100% acetonitrile in water with 0.05% trifluoroacetic acid, 7 min, column: Phenomenex Luna 5μ C18 50×21.2 mm).

EXAMPLE 1

(1R,2S,7R,8S)—N-{3-[3-(2-Chloro-4-fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide

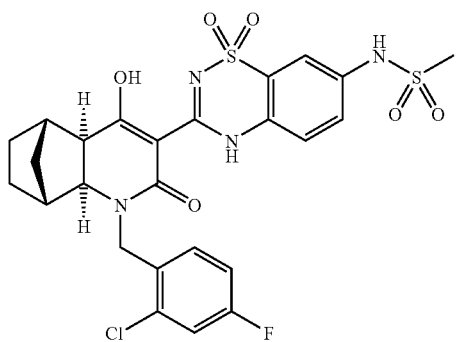

The compound of Example 1 was prepared according to the general experimental procedure A as described above.

LC-MS (ESI) calcd for $C_{25}H_{24}ClFN_4O_6S_2$ 594.08, found 595.2 [M+H$^+$].

EXAMPLE 2

N-{3-[(1S,2S,7R,8R)-3-(Chloro-4-fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide

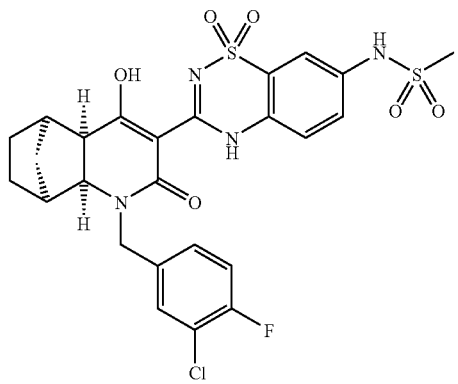

The compound of Example 2 was prepared according to the general experimental procedure A as described above.

$^1$H NMR (400 MHz, Acetone-d$_6$) δ: 1.39-1.52 (5H, m), 1.58-1.60 (1H, m), 2.75-2.83 (2H, m), 3.10 (3H, s), 3.29 (1H, dd, J$_1$=13.2 Hz, J$_2$=3.9 Hz), 3.93 (1H, dd, J$_1$=12.6 Hz, J$_2$=3.2 Hz), 4.20 (1H, d, J=15.7 Hz), 5.25 (1H, d, J=15.2 Hz), 7.24-7.28 (1H, m), 7.41-7.45 (1H, m), 7.55-7.59 (2H, m), 7.70 (1H, dd, J$_1$=8.8 Hz, J$_2$=2.4 Hz), 7.80 (1H, d, J=3.0 Hz), 8.96 (1H, s). LC-MS (ESI) calcd for $C_{25}H_{24}ClFN_4O_6S_2$ 594.08, found 595.3 [M+H$^+$].

EXAMPLE 3

N-{3-[(2S,7R)-6-Hydroxy-3-(3-methoxy-benzyl)-4-oxo-3-aza-tricyclo[6.2.2.0$^{2,7}$]dodec-5-en-5-yl]-1,1-dioxo-1,4-dihydro-1$\lambda^6$-benzo[1,2,4]thiadiazin-7-yl}-methanesulfonamide

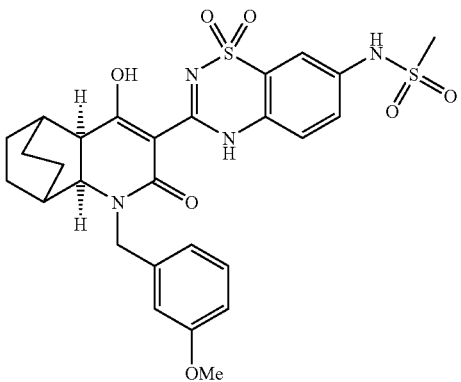

The compound of Example 3 was prepared according to the general experimental procedure A as described above.

$^1$H NMR (400 MHz, DMSO-d$_6$) δ: 1.40-1.44 (2H, m), 1.49-1.61 (6H, m), 1.93 (1H, s), 2.14 (1H, s), 3.06 (3H, s), 3.31 (1H, d, J=12.5 Hz), 3.73 (3H, s), 4.23 (1H, d, J=14.7 Hz), 5.05 (1H, d, J=14.6 Hz), 6.81-6.87 (3H, m), 7.24 (1H, t, J=7.5 Hz), 7.51 (1H, dd, $J_1$=9.5 Hz, $J_2$=2.3 Hz), 7.58-7.60 (2H, m), 10.19 (1H, s). LC-MS (ESI) calcd for $C_{27}H_{30}N_4O_7S_2$ 586.16, found 587.2 [M+H$^+$].

EXAMPLE 4

N-{3-[(2S,7R)-3-(2,4-Difluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide

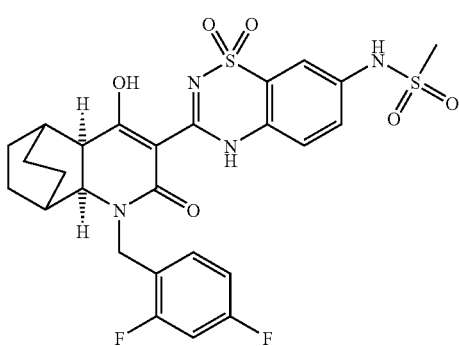

The compound of Example 4 was prepared according to the general experimental procedure A as described above.

$^1$H NMR (400 MHz, DMSO-d$_6$) δ: 1.36-1.47 (2H, m), 1.51-1.66 (6H, m), 1.90 (1H, s), 2.16 (1H, s), 3.06 (3H, s), 3.34 (1H, d, J=9.1 Hz), 3.80 (1H, d, J=11.8 Hz), 4.28 (1H, d, J=15.5 Hz), 5.04 (1H, d, J=15.8 Hz), 7.02-7.06 (1H, m), 7.21-7.26 (1H, m), 7.42 (1H, quartet, J=8.0 Hz), 7.51 (1H, dd, $J_1$=9.6 Hz, $J_2$=2.3 Hz), 7.58-7.60 (2H, m), 10.19 (1H, s). LC-MS (ESI) calcd for $C_{26}H_{26}F_2N_4O_6S_2$ 592.13, found 593.3 [M+H$^+$].

EXAMPLE 5

N-{3-[(2S,7R)-3-(2-Chloro-4-fluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide

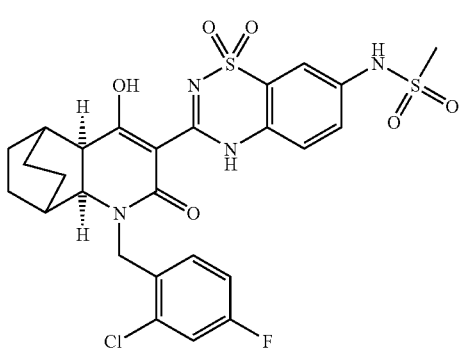

The compound of Example 5 was prepared according to the general experimental procedure A as described above.

$^1$H NMR (400 MHz, DMSO-d$_6$) δ: 1.39-1.44 (2H, m), 1.53-1.61 (6H, m), 1.88 (1H, s), 2.14 (1H, s), 3.06 (3H, s), 3.31 (1H, d, J=11.7 Hz), 3.79 (1H, d, J=10.9 Hz), 4.32 (1H, d, J=14.6 Hz), 4.97 (1H, d, J=15.7 Hz), 7.33-7.38 (2H, m), 7.50-7.54 (2H, m), 7.58-7.60 (2H, m), 10.19 (1H, s). LC-MS (ESI) calcd for $C_{26}H_{26}ClFN_4O_6S_2$ 608.10, found 609.2 [M+H$^+$].

EXAMPLE 6

N-{3-[(2S,7R)-3-(2-Bromo-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide

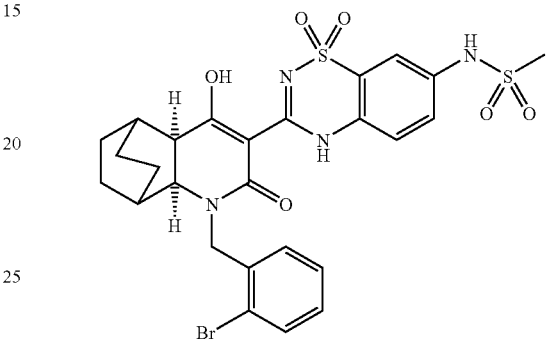

The compound of Example 6 was prepared according to the general experimental procedure A as described above.

$^1$H NMR (400 MHz, DMSO-d$_6$) δ: 1.40-1.47 (2H, m), 1.51-1.69 (6H, m), 1.87 (1H, s), 2.18 (1H, s), 3.05 (3H, s), 3.42 (1H, d, J=9.9 Hz), 3.80 (1H, d, J=11.6 Hz), 4.29 (1H, d, J=15.7 Hz), 5.03 (1H, d, J=16.4 Hz), 7.22 (1H, t, J=8.5 Hz), 7.30-7.37 (2H, m), 7.49 (1H, dd, $J_1$=8.4 Hz, $J_2$=2.3 Hz), 7.58-7.63 (3H, m), 10.19 (1H, s). LC-MS (ESI) calcd for $C_{26}H_{27}BrN_4O_6S_2$ 634.06, found 635.0 [M+H$^+$].

EXAMPLE 7

N-{3-[(2S,7R)-3-(4-Fluoro-3-methoxy-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide

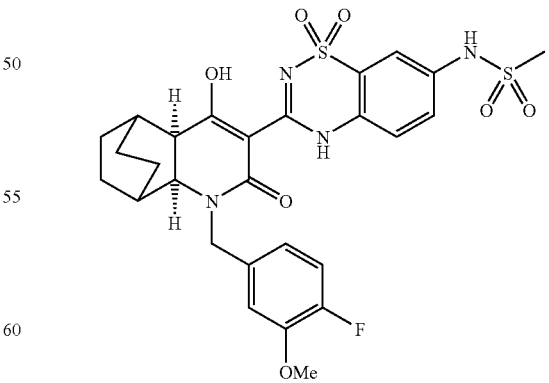

The compound of Example 7 was prepared according to the general experimental procedure A as described above.

$^1$H NMR (400 MHz, Acetone-d$_6$) δ: 1.43-1.52 (2H, m), 1.58-1.70 (6H, m), 2.02 (1H, s), 2.24 (1H, s), 3.10 (3H, s), 3.28-3.31 (1H, m), 3.84 (3H, s), 3.89 (1H, d, J=11.8 Hz), 4.29 (1H, d, J=15.4 Hz), 5.21 (1H, d, J=15.9 Hz), 6.91-6.94 (1H, m), 7.04-7.15 (2H, m), 7.55 (1H, d, J=9.3 Hz), 7.69 (1H, dd, $J_1$=8.7 Hz, $J_2$=2.4 Hz), 7.80 (1H, d, J=2.2 Hz), 8.97 (1H, bs). LC-MS (ESI) calcd for $C_{27}H_{29}FN_4O_7S_2$ 604.15, found 605.3 [M+H$^+$].

EXAMPLE 8

N-{3-[(2S,7R)-3-(3-Chloro-4-fluoro-benzyl)-6-hydroxy-4-oxo-3-aza-tricyclo[6.2.2.0$^{2,7}$]dodec-5-en-5-yl]-1,1-dioxo-1,4-dihydro-1$\lambda^6$-benzo[1,2,4]thiadiazin-7-yl}-methanesulfonamide

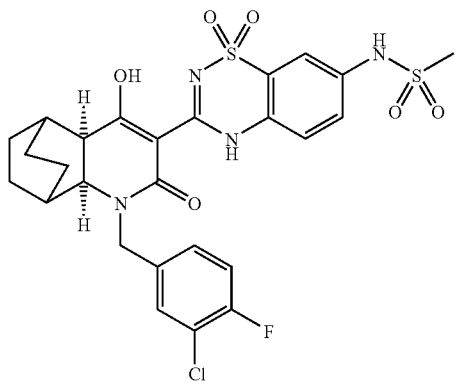

The compound of Example 8 was prepared according to the general experimental procedure A as described above.

$^1$H NMR (400 MHz, Acetone-d$_6$) δ: 1.46-1.52 (2H, m), 1.64-1.73 (6H, m), 2.01-2.02 (1H, m), 2.23-2.28 (1H, m), 3.10 (3H, s), 3.33 (1H, dd, $J_1$=11.3 Hz, $J_2$=2.7 Hz), 3.96 (1H, d, J=11.7 Hz), 4.37 (1H, d, J=15.5 Hz), 5.16 (1H, d, J=14.9 Hz), 7.23-7.27 (1H, m), 7.38-7.41 (1H, m), 7.53-7.57 (2H, m), 7.69 (1H, dd, $J_1$=9.3 Hz, $J_2$=2.4 Hz), 7.80 (1H, d, J=2.3 Hz), 8.96 (1H, s). LC-MS (ESI) calcd for $C_{26}H_{26}ClFN_4O_6S_2$ 608.10, found 609.2 [M+H$^+$].

EXAMPLE 9

N-{3-[(2S,7R)-3-(3,3-Dimethyl-butyl)-6-hydroxy-4-oxo-3-aza-tricyclo[6.2.2.0$^{2,7}$]dodec-5-en-5-yl]-1,1-dioxo-1,4-dihydro-1$\lambda^6$-benzo[1,2,4]thiadiazin-7-yl}-methanesulfonamide

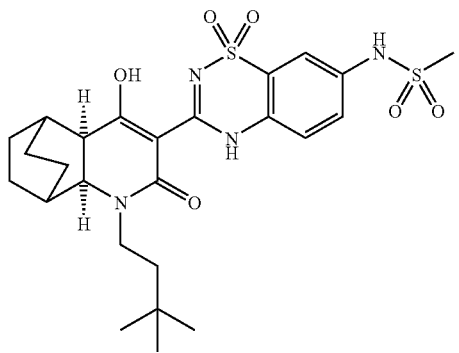

The compound of Example 9 was prepared according to the general experimental procedure A as described above. In this case, however, potassium iodide (~10 mg) was added to the reaction mixture for the alkylation step.

LC-MS (ESI) calcd for $C_{25}H_{34}N_4O_6S_2$ 550.19, found 551.4 [M+H$^+$].

EXAMPLE 10

N-{3-[(2S,7R)-3-(3,4-Difluoro-benzyl)-6-hydroxy-4-oxo-3-aza-tricyclo[6.2.2.0$^{2,7}$]dodec-5-en-5-yl]-1,1-dioxo-1,4-dihydro-1$\lambda^6$-benzo[1,2,4]thiadiazin-7-yl}-methanesulfonamide

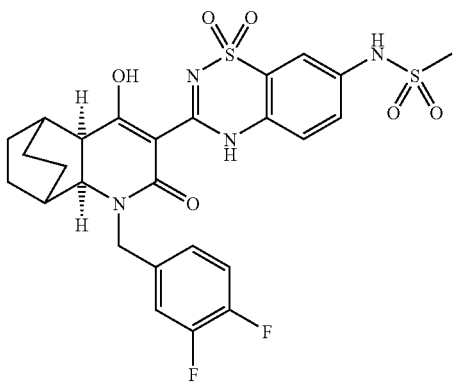

The compound of Example 10 was prepared according to the general experimental procedure B as described above.

$^1$H NMR (400 MHz, Acetone-d$_6$) δ: 1.45-1.51 (2H, m), 1.64-1.71 (6H, m), 2.00-2.04 (1H, m), 2.22-2.28 (1H, m), 3.09 (3H, s), 3.33 (1H, dd, $J_1$=12.2 Hz, $J_2$=2.9 Hz), 3.95 (1H, d, J=11.7 Hz), 4.37 (1H, d, J=15.7 Hz), 5.15 (1H, d, J=15.6 Hz), 7.20-7.30 (2H, m), 7.34-7.39 (1H, m), 7.54-7.56 (1H, m), 7.69 (1H, dd, $J_1$=9.3 Hz, $J_2$=2.4 Hz), 7.80 (1H, d, J=2.2 Hz), 8.97 (1H, s). LC-MS (ESI) calcd for $C_{26}H_{26}F_2N_4O_6S_2$ 592.13, found 593.3 [M+H$^+$].

EXAMPLE 11

N-{3-[(2S,7R)-3-(4-Fluoro-3-methyl-benzyl)-6-hydroxy-4-oxo-3-aza-tricyclo[6.2.2.0$^{2,7}$]dodec-5-en-5-yl]-1,1-dioxo-1,4-dihydro-1$\lambda^6$-benzo[1,2,4]thiadiazin-7-yl}-methanesulfonamide

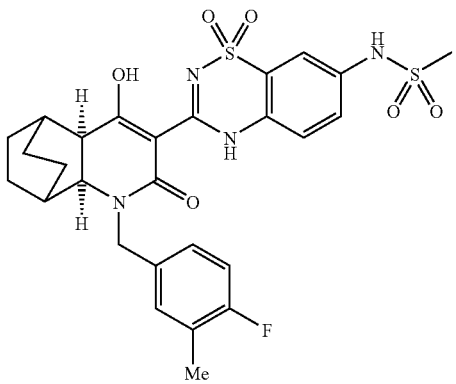

The compound of Example 11 was prepared according to the general experimental procedure B as described above.

¹H NMR (400 MHz, Acetone-$d_6$) δ: 1.45-1.58 (2H, m), 1.65-1.70 (6H, m), 2.01-2.04 (1H, m), 2.22-2.24 (4H, m), 3.10 (3H, s), 3.28 (1H, dd, $J_1$=11.6 Hz, $J_2$=3.3 Hz), 3.88 (1H, d, J=11.7 Hz), 4.23 (1H, d, J=15.4 Hz), 5.21 (1H, d, J=15.9 Hz), 6.97-7.02 (1H, m), 7.19-7.22 (1H, m), 7.26 (1H, d, J=8.0 Hz), 7.55 (1H, d, J=9.3 Hz), 7.69 (1H, dd, $J_1$=9.4 Hz, $J_2$=2.3 Hz), 7.80 (1H, d, J=2.2 Hz), 8.97 (1H, s). LC-MS (ESI) calcd for $C_{27}H_{29}FN_4O_6S_2$ 588.15, found 589.4 [M+H⁺].

EXAMPLE 12

N-{3-[(2S,7R)-3-Benzyl-6-hydroxy-4-oxo-3-aza-tricyclo[6.2.2.0$^{2,7}$]dodec-5-en-5-yl]-1,1-dioxo-1,2-dihydro-1λ$^6$-benzo[1,2,4]thiadiazin-7-yl}-methanesulfonamide

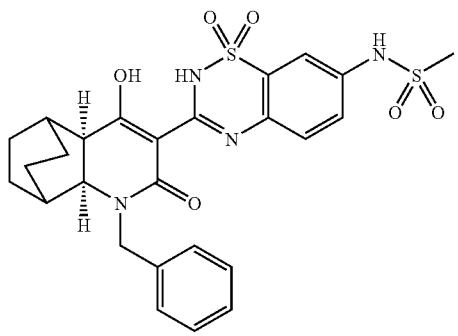

The compound of Example 12 was prepared according to the general experimental procedure A as described above.

¹H NMR (400 MHz, Acetone-$d_6$) δ: 1.49-1.73 (8H, m), 2.04-2.04 (1H, m), 2.26-2.27 (1H, m), 3.11 (3H, s), 3.26-3.32 (1H, m), 3.89 (1H, d, J=11.9 Hz), 4.32 (1H, d, J=14.7 Hz), 5.27 (1H, d, J=15.8 Hz), 7.26-7.38 (5H, m), 7.56 (1H, d, J=8.8 Hz), 7.70 (1H, dd, $J_1$=8.4 Hz, $J_2$=2.4 Hz), 7.81 (1H, d, J=2.4 Hz). LC-MS (ESI) calcd for $C_{26}H_{28}N_4O_6S_2$ 556.14, found 557.2 [M+H⁺].

EXAMPLE 13

(rac-di-exo,di-exo)-N-{3-[3-(4-Fluoro-benzyl)-6-hydroxy-4-oxo-3-aza-tetracyclo[6.3.1.0$^{2,7}$.0$^{9,11}$]dodec-5-en-5-yl]-1,1-dioxo-1,2-dihydro-1λ$^6$-benzo[1,2,4]thiadiazin-7-yl}-methanesulfonamide

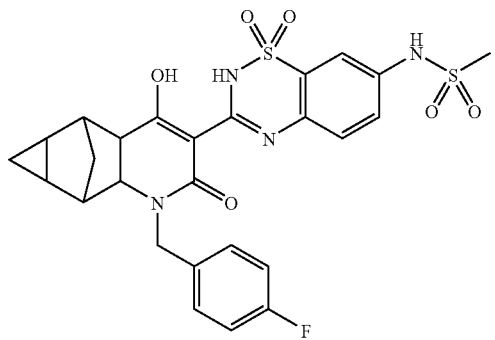

a) (rac-di-exo)-3-Aza-tricyclo[4.2.1.0$^{2,5}$]non-7-en-one

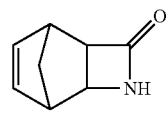

The title compound is reported in *Tetrahedron* 1984, 40, 12, 2385-2395, *Synlett* 2000, 1, 67-68 and *Chem. Commun.* 2006, 14, 1548-1550.

To a solution of bicyclo[2.2.1]hepta-2,5-diene (36.86 g, 0.40 mol) dissolved in anhydrous dichloromethane (20 mL) under an inert atmosphere of dry nitrogen was added solid anhydrous sodium carbonate (6.36 g, 60.0 mmol). The stirred suspension was cooled to 0° C. and chlorosulfonyl isocyanate (56.61 g, 0.40 mol) was slowly added dropwise over a period of 20 min. The mixture, kept at 0° C. for 2 h was gradually warmed to 25° C. and stirring was continued for 12 h. At this time the mixture was diluted with dichloromethane (40 mL) and added dropwise to a vigorously stirred mixture of sodium sulfite (145.6 g), disodium hydrogen phosphate (163 g), water (700 mL) and chloroform (580 mL) at 0° C. After the aqueous layer was separated, it was washed with dichloromethane (2×175 mL). The organic layers were combined and washed with water (100 mL), saturated aqueous brine solution (100 mL) and dried over anhydrous magnesium sulfate, filtered and concentrated in vacuo to afford the desired product, (rac-di-exo)-3-aza-tricyclo[4.2.1.0$^{2,5}$]non-7-en-one (45.9 g, 0.34 mol, 85%), as an off-white solid. ¹H NMR (400 MHz, CDCl₃) δ: 1.66 (1H, d, J=9.7 Hz), 1.82 (1H, d, J=10.2 Hz), 2.89-2.91 (1H, m), 2.94-2.97 (1H, m), 3.06 (1H, dd, $J_1$=3.9 Hz, $J_2$=1.5 Hz), 3.51 (1H, d, J=3.8 Hz), 5.97 (1H, bs), 6.13 (1H, dd, $J_1$=5.5 Hz, $J_2$=3.1 Hz), 6.25 (1H, dd, $J_1$=5.3 Hz, $J_2$=3.2 Hz).

b) (rac-di-exo)-3-(4-Fluoro-benzyl)-3-aza-tricyclo[4.2.1.0$^{2,5}$]non-7-en-4-one

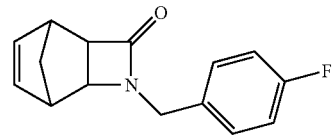

(rac-di-exo)-3-Aza-tricyclo[4.2.1.0$^{2,5}$]non-7-en-one (0.676 g, 5.0 mmol), 4-fluorobenzyl bromide (1.04 g, 5.5 mmol), and tetrabutylammonium hydrogen sulfate (0.17 g, 0.5 mmol) were dissolved in dichloromethane (8 mL) and cooled to 0° C. The solution was vigorously stirred and 50% aqueous sodium hydroxide solution (7.6 mL) was added dropwise over a period of 30 min. The biphasic mixture was warmed to 25° C. and stirred for an additional 3 h. Water (19 mL) was added and the layers were separated. Further extraction of the aqueous layer was done with dichloromethane (2×5 mL). The organic layers were combined, dried over anhydrous magnesium sulfate, filtered and concentrated in vacuo to afford a thick yellow oil. Addition of ethyl acetate to the oil precipitated a pale yellow solid. The solids were filtered, washed with ethyl acetate. The ethyl acetate solution was concentrated in vacuo and the residue was purified by flash column chromatography (Teledyne Isco RediSep column; 0-100% ethyl acetate in hexanes) to afford the desired product, (rac-di-exo)-3-(4-fluoro-benzyl)-3-aza-tricyclo[4.2.1.0$^{2,5}$]non-7-en-4-one (0.756 g, 3.1 mmol, 62%), as a pale yellow oil. ¹H NMR (400 MHz, CDCl₃) δ: 1.53-1.60 (2H, m), 2.69 (1H, s), 2.96 (1H, s), 3.02 (1H, d, J=3.8 Hz), 3.38 (1H, d, J=3.8 Hz), 4.19 (1H, d, J=14.8 Hz), 4.47 (1H, d, J=14.8 Hz), 6.01 (1H, dd, $J_1$=5.6 Hz, $J_2$=5.5 Hz), 6.22 (1H, dd, $J_1$=5.3 Hz, $J_2$=5.3 Hz), 7.00-7.06 (2H, m), 7.24-7.29 (2H, m).

c) (rac-di-exo,di-exo)-3-(4-Fluoro-benzyl)-3-aza-tetracyclo[4.3.1.0$^{2,5}$.0$^{7,9}$]decan-4-one

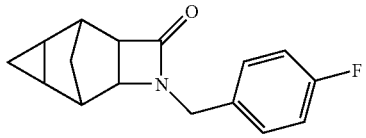

To an Erlenmeyer flask equipped with a rubber stopper (rac-di-exo)-3-(4-fluoro-benzyl)-3-aza-tricyclo[4.2.1.0$^{2,5}$]non-7-en-4-one (0.467 g, 1.92 mmol) was dissolved in anhydrous diethyl ether (8 mL). Palladium acetate (9.0 mg, 40 µmol) is added and the mixture is cooled to 0° C. To this stirred mixture is carefully added dropwise an ice cold solution of diazomethane in diethyl ether (5.76 mmol prepared from N-methyl-N-nitro-N-nitrosoguanidine and 50% aqueous potassium hydroxide solution). The yellow solution was stirred at 0° C. for 2 h. Any excess of diazomethane was evaporated by a gentle stream of nitrogen gas. The solution was further concentrated in vacuo and the residue was filtered through a plug of silica gel (Merck silica gel 60, 40-63 µm). The silica gel was washed with 10-60% ethyl acetate in hexanes and the washing were collected and concentrated in vacuo to afford the desired product, (rac-di-exo,di-exo)-3-(4-fluoro-benzyl)-3-aza-tetracyclo[4.3.1.0$^{2,5}$.0$^{7,9}$]decan-4-one (quantitative yield) as a pale yellow oil. $^1$H NMR (400 MHz, CDCl$_3$) δ: 0.27 (1H, quartet, J=7.1 Hz), 0.59-0.64 (1H, m), 0.67 (1H, dt, $J_1$=6.3 Hz, $J_2$=3.1 Hz), 0.74-0.79 (1H, m), 0.90 (2H, quartet, J=11.4 Hz), 2.21 (1H, s), 2.50 (1H, t, J=1.5 Hz), 3.17-3.18 (1H, m), 3.44 (1H, d, J=4.1 Hz), 4.15 (1H, d, J=14.8 Hz), 4.40 (1H, d, J=14.8 Hz), 6.99-7.05 (2H, m), 7.22-7.27 (2H, m).

d) (rac-di-exo,di-exo)-7-(4-Fluoro-benzylamino)-tricyclo[3.2.1.0$^{2,4}$]octane-6-carboxylic acid ethyl ester

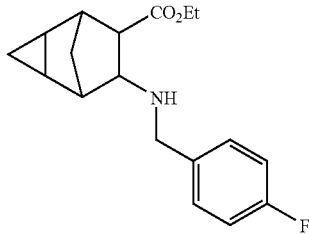

(rac-di-exo,di-exo)-3-(4-Fluoro-benzyl)-3-aza-tetracyclo[4.3.1.0$^{2,5}$.0$^{7,9}$]decan-4-one (0.257 g, 1.0 mmol) was dissolved in absolute ethanol (2 mL) and cooled to 0° C. To this was added a 2.5 M solution of hydrochloric acid in ethanol (0.8 mL). Thin layer chromatography (Merck silica gel 60, 40-63 µm; 50% ethyl acetate in hexanes) indicated the presence of starting material after stirring the mixture at 25° C. and then 40° C. for 2 h. A 4.0 M solution of hydrochloric acid in 1,4-dioxane (2×0.25 mL) was therefore added and the mixture was stirred at 60° C. for 14 h. Thin layer chromatography (Merck silica gel 60, 40-63 µm; 50% ethyl acetate in hexanes) and LC-MS showed the amino ester was formed with almost complete consumption of starting material. The solution was concentrated in vacuo and diethyl ether (7 mL) was added. The hydrochloride salt did not solidify therefore the oily residue was taken up in excess ethyl acetate and washed several times with a saturated aqueous sodium bicarbonate solution. The aqueous layers were back-extracted with ethyl acetate. The organic layers were combined, dried over anhydrous magnesium sulfate, filtered and was concentrated in vacuo to afford the desired product, (rac-di-exo,di-exo)-7-(4-fluoro-benzylamino)-tricyclo[3.2.1.0$^{2,4}$]octane-6-carboxylic acid ethyl ester, as an oil in ~95%. $^1$H NMR (400 MHz, CDCl$_3$) δ: 0.14 (1H, quartet, J=6.8 Hz), 0.56-0.59 (1H, m), 0.69 (1H, d, J=2.9 Hz), 0.71 (1H, d, J=3.0 Hz), 0.94 (1H, d, J=11.8 Hz), 1.28 (3H, t, J=7.0 Hz), 1.47 (1H, d, J=11.6 Hz), 2.33 (1H, s), 2.46 (1H, s), 2.72 (1H, dd, $J_1$=8.1 Hz, $J_2$=2.1 Hz), 3.08 (1H, d, J=7.8 Hz), 3.68 (1H, s), 3.70 (1H, d, J=11.1 Hz), 3.81 (1H, d, J=13.4 Hz), 4.14 (2H, quartet, J=7.0 Hz), 6.98 (2H, t, J=8.9 Hz), 7.23-7.29 (2H, m). LC-MS (ESI) calculated for $C_{18}H_{22}FNO_2$ 303.16, found 304.2 [M+H$^+$].

e) (rac-di-exo,di-exo)-N-{3-[3-(4-Fluoro-benzyl)-6-hydroxy-4-oxo-3-aza-tetracyclo[6.3.1.0$^{2,7}$.0$^{9,11}$]dodec-5-en-5-yl]-1,1-dioxo-1,2-dihydro-1λ$^6$-benzo[1,2,4]thiadiazin-7-yl}-methanesulfonamide

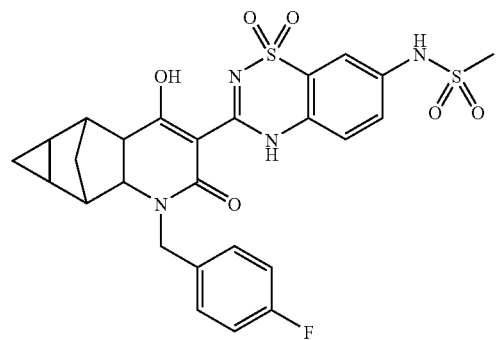

Under a dry nitrogen atmosphere (rac-di-exo)-7-(4-fluoro-benzylamino)-tricyclo[3.2.1.0$^{2,4}$]octane-6-carboxylic acid ethyl ester (0.135 g, 0.44 mmol) was dissolved in N,N-dimethylformamide (1.4 mL). To this stirred solution was added [7-(methanesulfonylamino-methyl)-1,1-dioxo-1,4-dihydro-1λ$^6$-benzo[1,2,4]thiadiazin-3-yl]-acetic acid (0.148 g, 0.44 mmol) and 1-(3-dimethylaminopropyl)-3-ethylcarbodiimide hydrochloride (0.128 g, 0.67 mmol). After 1 h, triethylamine (0.27 g, 2.67 mmol) was added and the stirred mixture was heated to 75° C. for a total of 20 h. The dark mixture was cooled to 25° C. and 1.0 M aqueous hydrochloric acid solution (12 mL) was added where upon a tan solid formed. The solids were filtered, washed with water, air-dried. The solids were triturated with ethyl acetate and hexane. The least pure fraction was purified by flash column chromatography (Teledyne Isco RediSep column; 0-5% methanol in dichloromethane. A total of 0.2 g (80% yield) of the desired product, (rac-di-exo,di-exo)-N-{3-[3-(4-Fluoro-benzyl)-6-hydroxy-4-oxo-3-aza-tetracyclo[6.3.1.0$^{2,7}$.0$^{9,11}$]dodec-5-en-5-yl]-1,1-dioxo-1,2-dihydro-1λ$^6$-benzo[1,2,4]thiadiazin-7-yl}-methanesulfonamide was isolated as an off-white to a beige solid. $^1$H NMR (400 MHz, DMSO-d$_6$) δ: 0.14-0.20 (1H, m), 0.48-0.57 (1H, m), 0.74-1.07 (4H, m), 2.57 (1H, s), 2.69 (1H, s), 3.06 (3H, s), 3.12 (1H, d, J=7.8 Hz), 3.60 (1H, d, J=8.8 Hz), 4.46 (1H, d, J=15.9 Hz), 4.97 (1H, d, J=15.3 Hz), 7.16 (2H, t, J=8.6 Hz), 7.35 (2H, t, J=6.6 Hz), 7.50 (1H, dd, $J_1$=8.9 Hz, $J_2$=2.1 Hz), 7.56-7.58 (2H, m), 10.18 (1H, s). LC-MS (ESI) calculated for $C_{26}H_{25}FN_4O_6S_2$ 572.12, found 573.1 [M+H$^+$].

EXAMPLE 14

N-{3-[(2S,7R)-3-(3-Fluoro-benzyl)-6-hydroxy-4-oxo-3-aza-tricyclo[6.2.2.0$^{2,7}$]dodec-5-en-5-yl]-1,1-dioxo-1,2-dihydro-1λ$^6$-benzo[1,2,4]thiadiazin-7-yl}-methanesulfonamide

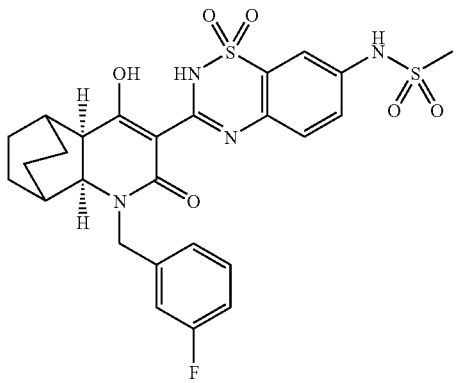

The compound of Example 14 was prepared according to the general experimental procedure A as described above.

$^1$H NMR (400 MHz, Acetone-d$_6$) δ: 1.29-1.73 (8H, m), 1.98-2.03 (1H, m), 2.27-2.30 (1H, m), 3.10 (3H, s), 3.24-3.33 (1H, m), 3.93 (1H, d, J=9.4 Hz), 4.39 (1H, d, J=15.4 Hz), 5.21 (1H, d, J=15.6 Hz), 6.99-7.06 (1H, m), 7.15 (1H, d, J=8.6 Hz), 7.21 (1H, d, J=7.0 Hz), 7.34-7.40 (1H, m), 7.50-7.57 (1H, m), 7.69 (1H, d, J=8.8 Hz), 7.80 (1H, s). LC-MS (ESI) calcd for C$_{26}$H$_{27}$FN$_4$O$_6$S$_2$ 574.14, found 575.3 [M+H$^+$].

EXAMPLE 15

N-{3-[(2S,7R)-3-Cyclohexylmethyl-6-hydroxy-4-oxo-3-aza-tricyclo[6.2.2.0$^{2,7}$]dodec-5-en-5-yl]-1,1-dioxo-1,2-dihydro-1λ$^6$-benzo[1,2,4]thiadiazin-7-yl}-methanesulfonamide

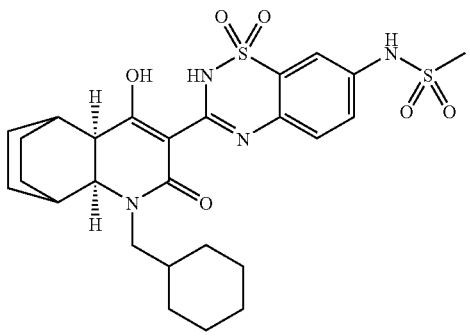

The compound of Example 15 was prepared according to the general experimental procedure B as described above.

$^1$H NMR (400 MHz, Acetone-d$_6$) δ: 0.94-1.89 (17H, m), 1.97-2.00 (1H, m), 2.21-2.24 (1H, m), 2.69-2.74 (1H, m), 3.09 (3H, s), 3.32-3.35 (1H, m), 3.93-3.98 (2H, m), 7.54 (1H, d, J=9.1 Hz), 7.68-7.71 (1H, m), 7.79 (1H, d, J=2.4 Hz). LC-MS (ESI) calcd for C$_{26}$H$_{34}$N$_4$O$_6$S$_2$ 562.19, found 563.5 [M+H$^+$].

EXAMPLE 16

N-{3-[(2S,7R)-6-Hydroxy-4-oxo-3-thiophen-2-ylmethyl-3-aza-tricyclo[6.2.2.0$^{2,7}$]dodec-5-en-5-yl]-1,1-dioxo-1,2-dihydro-1λ$^6$-benzo[1,2,4]thiadiazin-7-yl}-methanesulfonamide

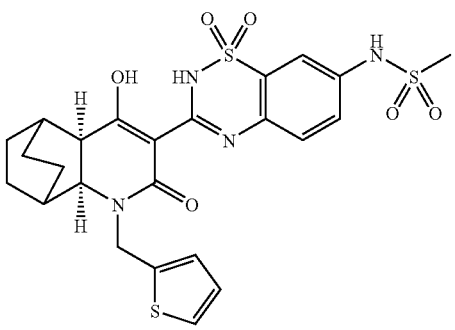

The compound of Example 16 was prepared according to the general experimental procedure B as described above.

$^1$H NMR (400 MHz, DMSO-d$_6$) δ: 1.36-1.66 (8H, m), 2.01 (1H, bs), 2.12 (1H, bs), 3.16 (3H, s), 3.23-3.26 (1H, m), 3.82 (1H, d, J=10.7 Hz), 4.47-4.51 (1H, m), 5.08-5.12 (1H, m), 6.95 (1H, dd, J$_1$=5.1 Hz, J$_2$=3.4 Hz), 7.10 (1H, d, J=3.3 Hz), 7.42 (1H, d, J=4.7 Hz), 7.52 (1H, dd, J$_1$=8.3 Hz, J$_2$=2.3 Hz), 7.58-7.62 (2H, m), 10.18 (1H, s). LC-MS (ESI) calcd for C$_{24}$H$_{26}$N$_4$O$_6$S$_3$ 562.10, found 563.3 [M+H$^+$].

EXAMPLE 17

N-{3-[(2S,7R)-6-Hydroxy-3-(2-methyl-benzyl)-4-oxo-3-aza-tricyclo[6.2.2.0$^{2,7}$]dodec-5-en-5-yl]-1,1-dioxo-1,2-dihydro-1λ$^6$-benzo[1,2,4]thiadiazin-7-yl}-methanesulfonamide

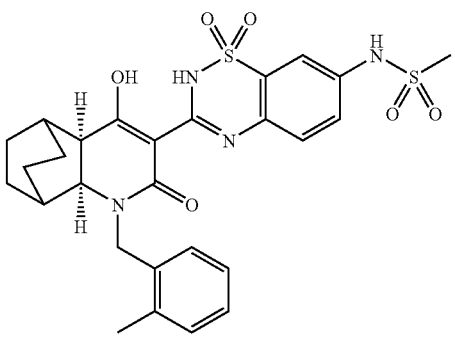

The compound of Example 17 was prepared according to the general experimental procedure A as described above.

$^1$H NMR (400 MHz, Acetone-d$_6$) δ: 1.36-1.78 (8H, m), 2.02-2.04 (1H, m), 2.28-2.30 (1H, m), 2.33 (3H, s), 3.10 (3H, s), 3.28-3.41 (1H, m), 3.81 (1H, d, J=13.4 Hz), 4.24 (1H, d, J=14.6 Hz), 5.31 (1H, d, J=15.6 Hz), 7.16-7.24 (5H, m), 7.54

(1H, d, J=7.9 Hz), 7.69 (1H, dd, J$_1$=8.5 Hz, J$_2$=2.2 Hz), 7.80 (1H, d, J=2.3 Hz). LC-MS (ESI) calcd for C$_{27}$H$_{30}$N$_4$O$_6$S$_2$ 570.16, found 571.1 [M+H$^+$].

EXAMPLE 18

N-{3-[(2S,7R)-6-Hydroxy-4-oxo-3-(2,3,4-trifluoro-benzyl)-3-aza-tricyclo[6.2.2.0$^{2,7}$]dodec-5-en-5-yl]-1,1-dioxo-1,2-dihydro-1λ$^6$-benzo[1,2,4]thiadiazin-7-yl}-methanesulfonamide

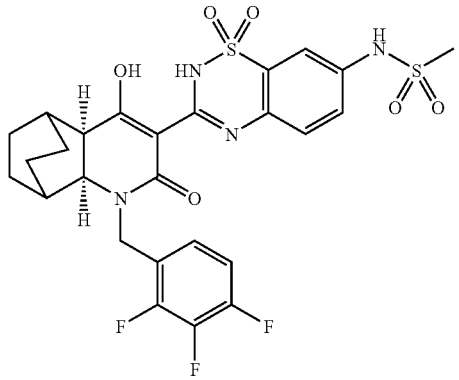

The compound of Example 18 was prepared according to the general experimental procedure A as described above.
$^1$H NMR (400 MHz, Acetone-d$_6$) δ: 1.48-1.57 (2H, m), 1.68-1.77 (6H, m), 2.03-2.03 (1H, m), 2.28-2.29 (1H, m), 3.10 (3H, s), 3.29-3.36 (1H, m), 4.00 (1H, d, J=11.7 Hz), 4.42 (1H, d, J=15.9 Hz), 5.23 (1H, d, J=15.6 Hz), 7.11-7.18 (1H, m), 7.28-7.35 (1H, m), 7.53 (1H, d, J=8.8 Hz), 7.69 (1H, dd, J$_1$=9.5 Hz, J$_2$=2.3 Hz), 7.80 (1H, d, J=2.4 Hz). LC-MS (ESI) calcd for C$_{26}$H$_{25}$F$_3$N$_4$O$_6$S$_2$ 610.12, found 611.1 [M+H$^+$].

EXAMPLE 19

N-{3-[(1S,2S,7R,8R)-3-(4-Fluoro-3-methyl-benzyl)-6-hydroxy-4-oxo-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide

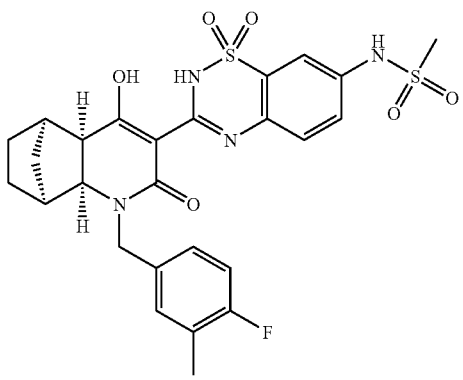

The compound of Example 19 was prepared according to the general experimental procedure B as described above.
$^1$H NMR (400 MHz, Acetone-d$_6$) δ: 1.40-1.58 (6H, m), 2.23 (3H, d, J=2.4 Hz), 2.77 (2H, bs), 3.10 (3H, s), 3.25 (1H, dd, J$_1$=12.4 Hz, J$_2$=3.9 Hz), 3.86 (1H, dd, J$_1$=12.3 Hz, J$_2$=3.7 Hz), 4.06 (1H, d, J=15.6 Hz), 5.29 (1H, d, J=15.5 Hz), 6.98-7.03 (1H, m), 7.22-7.26 (1H, m), 7.30 (1H, d, J=6.9 Hz), 7.56 (1H, d, J=9.6 Hz), 7.70 (1H, dd, J$_1$=8.9 Hz, J$_2$=2.5 Hz), 7.80 (1H, d, J=2.3 Hz). LC-MS (ESI) calcd for C$_{26}$H$_{27}$FN$_4$O$_6$S$_2$ 574.13, found 575.3 [M+H$^+$].

EXAMPLE 20

N-{3-[(1S,2S,7R,8R)-(3-Benzyl-6-hydroxy-4-oxo-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide

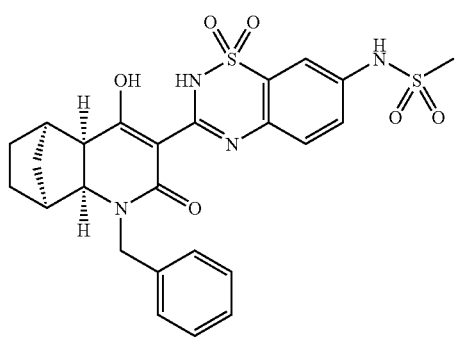

The compound of Example 20 was prepared according to the general experimental procedure A as described above.
$^1$H NMR (400 MHz, Acetone-d$_6$) δ: 1.41-1.58 (6H, m), 2.75-2.82 (2H, m), 3.10 (3H, s), 3.24-3.28 (1H, m), 3.83-3.87 (1H, m), 4.10 (1H, d, J=14.8 Hz), 5.36 (1H, d, J=15.0 Hz), 7.25-7.39 (5H, m), 7.57 (1H, d, J=9.1 Hz), 7.70 (1H, dd, J$_1$=8.5 Hz, J$_2$=2.3 Hz), 7.80 (1H, d, J=2.3 Hz), 8.95 (1H, s). LC-MS (ESI) calcd for C$_{25}$H$_{26}$N$_4$O$_6$S$_2$ 542.13, found 543.2 [M+H$^+$].

EXAMPLE 21

N-{3-[(1R,2S,7R,8S)-3-(3-Fluoro-benzyl)-6-hydroxy-4-oxo-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide

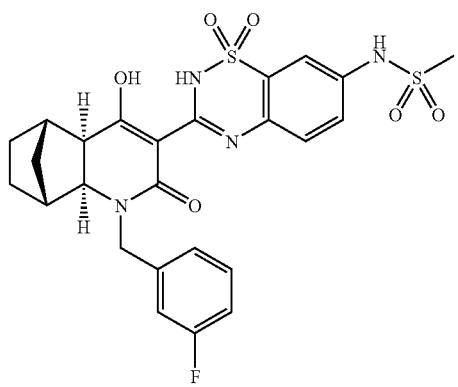

The compound of Example 21 was prepared according to the general experimental procedure B as described above.

$^1$H NMR (400 MHz, DMSO-d$_6$) δ: 1.22-1.26 (2H, m), 1.40-1.62 (4H, m), 2.64-2.64 (1H, m), 3.03-3.05 (1H, m), 3.05 (3H, s), 3.56 (1H, d, J=9.4 Hz), 4.49 (1H, d, J=16.4 Hz), 4.94 (1H, d, J=16.4 Hz), 7.04-7.13 (3H, m), 7.34-7.39 (1H, m), 7.49 (1H, dd, J$_1$=8.6 Hz, J$_2$=2.4 Hz), 7.54-7.57 (2H, m), 10.16 (1H, s). LC-MS (ESI) calcd for C$_{25}$H$_{25}$FN$_4$O$_6$S$_2$ 560.12, found 561.2 [M+H$^+$].

EXAMPLE 22

N-{3-[(1S,2S,7R,8R)-6-Hydroxy-4-oxo-3-(1-trifluoromethyl-cyclopropylmethyl)-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide

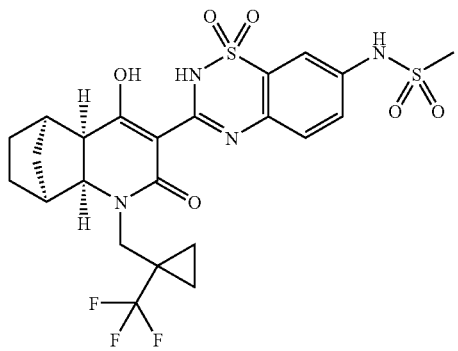

The compound of Example 22 was prepared according to the general experimental procedure A as described above.

$^1$H NMR (400 MHz, Acetone-d$_6$) δ: 0.94-1.15 (4H, m), 1.25-1.55 (5H, m), 1.67-1.72 (1H, m), 2.78-2.85 (2H, m), 2.98 (1H, d, J=14.6 Hz), 3.09 (3H, s), 3.32-3.36 (1H, m), 4.16-4.20 (1H, m), 4.75 (1H, d, J=15.0 Hz), 7.54 (1H, d, J=8.8 Hz), 7.70 (1H, dd, J$_1$=8.9 Hz, J$_2$=4.5 Hz), 7.79 (1H, d, J=2.4 Hz), 8.96 (1H, s). LC-MS (ESI) calcd for C$_{23}$H$_{25}$F$_3$N$_4$O$_6$S$_2$ 574.11, found 575.3 [M+H$^+$].

EXAMPLE 23

N-{3-[(1S,2S,7R,8R)-3-(3,4-Difluoro-benzyl)-6-hydroxy-4-oxo-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide

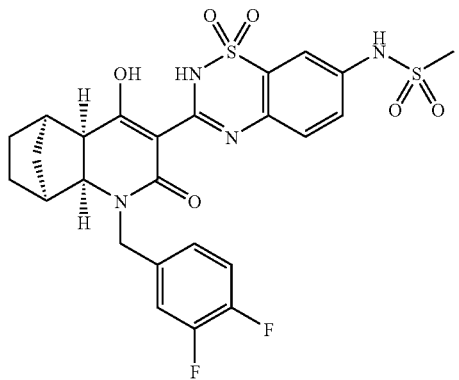

The compound of Example 23 was prepared according to the general experimental procedure B as described above.

$^1$H NMR (400 MHz, Acetone-d$_6$) δ: 1.38-1.53 (5H, m), 1.55-1.60 (1H, m), 2.78-2.82 (2H, m), 3.10 (3H, s), 3.28 (1H, dd, J$_1$=11.9 Hz, J$_2$=3.2 Hz), 3.92 (1H, dd, J$_1$=12.4 Hz, J$_2$=3.0 Hz), 4.20 (1H, d, J=14.6 Hz), 5.24 (1H, d, J=15.3 Hz), 7.25-7.31 (2H, m), 7.37-7.42 (1H, m), 7.56 (1H, d, J=8.8 Hz), 7.70 (1H, dd, J$_1$=9.3 Hz, J$_2$=2.3 Hz), 7.80 (1H, d, J=2.3 Hz), 8.97 (1H, s). LC-MS (ESI) calcd for C$_{25}$H$_{24}$F$_2$N$_4$O$_6$S$_2$ 578.11 found 579.1 [M+H$^+$].

EXAMPLE 24

N-{3-[(1R,2S,7R,8S)-6-Hydroxy-4-oxo-3-(2,3,4-trifluoro-benzyl)-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide

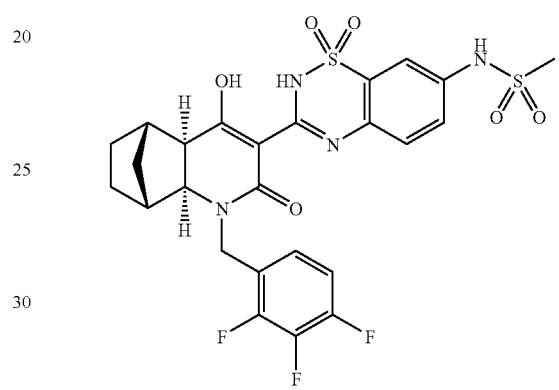

The compound of Example 24 was prepared according to the general experimental procedure A as described above.

$^1$H NMR (400 MHz, Acetone-d$_6$) δ: 1.32-1.38 (2H, m), 1.50-1.56 (1H, m), 1.62-1.78 (3H, m), 2.66 (1H, d, J=4.0 Hz), 2.77-2.78 (1H, m), 3.07 (1H, d, J=9.3 Hz), 3.10 (3H, s), 3.77 (1H, d, J=9.3 Hz), 4.57 (1H, d, J=15.7 Hz), 5.14 (1H, d, J=15.5 Hz), 7.12-7.19 (1H, m), 7.25-7.31 (1H, m), 7.52 (1H, d, J=8.4 Hz), 7.69 (1H, dd, J$_1$=9.6 Hz, J$_2$=3.1 Hz), 7.80 (1H, d, J=2.4 Hz). LC-MS (ESI) calcd for C$_{25}$H$_{23}$F$_3$N$_4$O$_6$S$_2$ 596.10, found 597.2 [M+H$^+$].

EXAMPLE 25

N-{3-[(1R,2S,7R,8S)-6-Hydroxy-4-oxo-3-thiophen-3-ylmethyl-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide

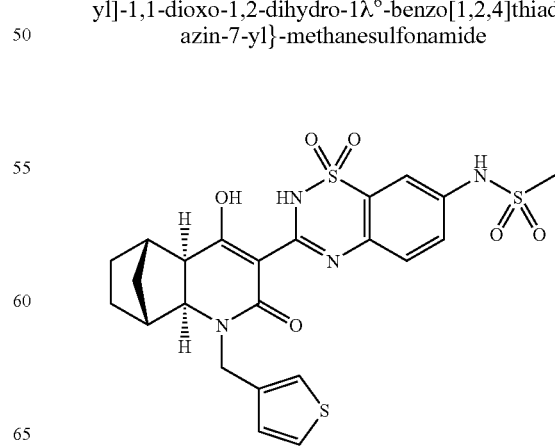

The compound of Example 25 was prepared according to the general experimental procedure B as described above.

$^1$H NMR (400 MHz, Acetone-d$_6$) δ: 1.26-1.35 (2H, m), 1.48-1.72 (4H, m), 2.64-2.65 (1H, m), 2.74-2.75 (1H, m), 3.02 (1H, d, J=9.2 Hz), 3.09 (3H, s), 3.68-3.70 (1H, m), 4.47 (1H, d, J=15.9 Hz), 5.08 (1H, d, J=15.8 Hz), 7.11-7.12 (1H, m), 7.39-7.43 (2H, m), 7.55 (1H, d, J=9.3 Hz), 7.69 (1H, dd, J$_1$=9.4 Hz, J$_2$=2.3 Hz), 7.79 (1H, d, J=2.3 Hz), 8.97 (1H, s). LC-MS (ESI) calcd for C$_{23}$H$_{24}$N$_4$O$_6$S$_3$ 548.09, found 549.3 [M+H$^+$].

EXAMPLE 26

N-{3-[2S,7R)-6-Hydroxy-4-oxo-3-(2,4,5-trifluoro-benzyl)-3-aza-tricyclo[6.2.2.0$^{2,7}$]dodec-5-en-5-yl]-1,1-dioxo-1,2-dihydro-1λ$^6$-benzo[1,2,4]thiadiazin-7-yl}-methanesulfonamide

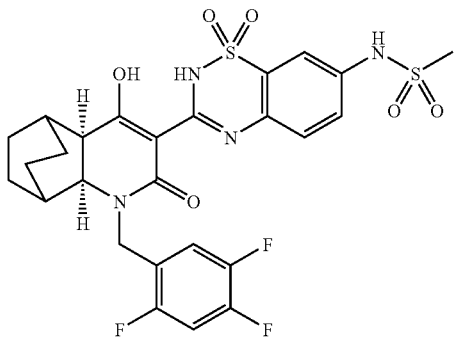

The compound of Example 26 was prepared according to the general experimental procedure A as described above.

$^1$H NMR (400 MHz, Acetone-d$_6$) δ: 1.48-1.57 (2H, m), 1.68-1.75 (6H, m), 2.01-2.02 (1H, m), 2.28-2.29 (1H, m), 3.10 (3H, s), 3.34-3.42 (1H, m), 4.03 (1H, d, J=11.7 Hz), 4.41 (1H, d, J=15.6 Hz), 5.13 (1H, d, J=16.2 Hz), 7.25-7.31 (1H, m), 7.43-7.50 (1H, m), 7.54 (1H, d, J=9.1 Hz), 7.70 (1H, dd, J$_1$=8.9 Hz, J$_2$=2.5 Hz), 7.80 (1H, d, J=2.3 Hz). LC-MS (ESI) calcd for C$_{26}$H$_{25}$F$_3$N$_4$O$_6$S$_2$ 610.11, found 611.2 [M+H$^+$].

EXAMPLE 27

N-{3-[(1R,2S,7R,8S)-6-Hydroxy-4-oxo-3-thiophen-2-ylmethyl-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide

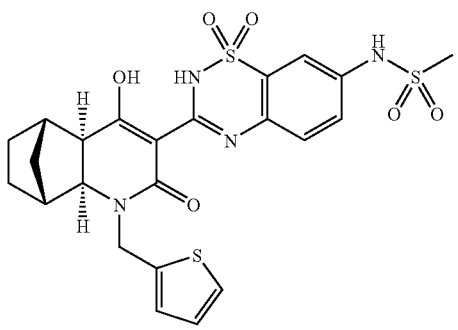

The compound of Example 27 was prepared according to the general experimental procedure B as described above.

$^1$H NMR (400 MHz, Acetone-d$_6$) δ: 1.27-1.37 (2H, m), 1.50-1.54 (1H, m), 1.61-1.73 (3H, m), 2.71-2.75 (2H, m), 3.01-3.04 (1H, m), 3.10 (3H, s), 3.73 (1H, d, J=9.3 Hz), 4.61 (1H, d, J=15.8 Hz), 5.24 (1H, d, J=15.8 Hz), 6.96-6.98 (1H, m), 7.13 (1H, d, J=3.0 Hz), 7.37 (1H, d, J=4.8 Hz), 7.57 (1H, d, J=9.3 Hz), 7.70 (1H, dd, J$_1$=9.3 Hz, J$_2$=2.7 Hz), 7.79 (1H, d, J=2.4 Hz), 8.99 (1H, s). LC-MS (ESI) calcd for C$_{23}$H$_{24}$N$_4$O$_6$S$_3$ 548.09, found 549.3 [M+H$^+$].

EXAMPLE 28

N-{3-[(1R,2S,7R,8S)-(3-Cyclohexylmethyl-6-hydroxy-4-oxo-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide

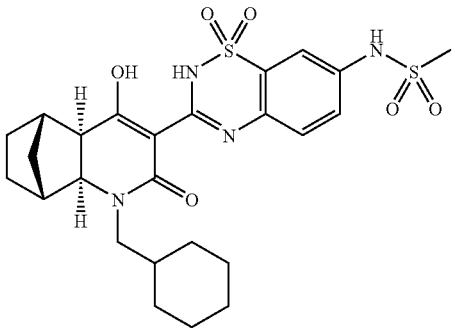

The compound of Example 28 was prepared according to the general experimental procedure A as described above.

$^1$H NMR (400 MHz, Acetone-d$_6$) δ: 0.92-1.81 (16H, m), 1.87-1.95 (1H, m), 2.63 (1H, d, J=4.0 Hz), 2.71 (1H, d, J=3.2 Hz), 2.81-2.86 (1H, m), 3.05-3.08 (1H, m), 3.09 (3H, s), 3.73 (1H, d, J=9.4 Hz), 3.90-3.95 (1H, m), 7.53 (1H, d, J=8.4 Hz), 7.68 (1H, dd, J$_1$=8.4 Hz, J$_2$=2.4 Hz), 7.78 (1H, d, J=2.4 Hz), 8.95 (1H, s). LC-MS (ESI) calcd for C$_{25}$H$_{32}$N$_4$O$_6$S$_2$ 548.18, found 549.4 [M+H$^+$].

EXAMPLE 29

N-{3-[(1S,2S,7R,8R)-6-Hydroxy-3-(2-methyl-benzyl)-4-oxo-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide

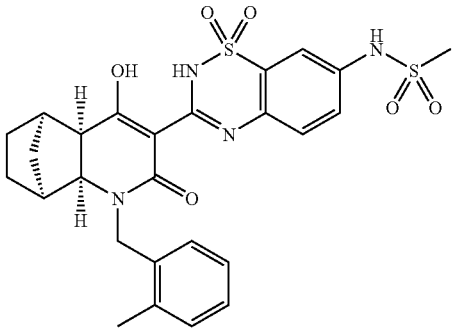

The compound of Example 29 was prepared according to the general experimental procedure A as described above.

$^1$H NMR (400 MHz, Acetone-d$_6$) δ: 1.47-1.58 (6H, m), 2.34 (3H, s), 2.79-2.81 (2H, m), 3.11 (3H, s), 3.29-3.32 (1H, m), 3.79 (1H, dd, J$_1$=12.5 Hz, J$_2$=3.0 Hz), 4.01 (1H, d, J=14.7 Hz), 5.48 (1H, d, J=15.5 Hz), 7.14-7.21 (3H, m), 7.25 (1H, d, J=8.0 Hz), 7.56 (1H, d, J=8.5 Hz), 7.70 (1H, dd, J$_1$=8.5 Hz, J$_2$=2.3 Hz), 7.81 (1H, d, J=2.3 Hz). LC-MS (ESI) calcd for C$_{26}$H$_{28}$N$_4$O$_6$S$_2$ 556.14, found 557.2 [M+H$^+$].

EXAMPLE 30

N-{3-[(1S,2S,7R,8R)-3-(3-Fluoro-benzyl-6-hydroxy-4-oxo-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide

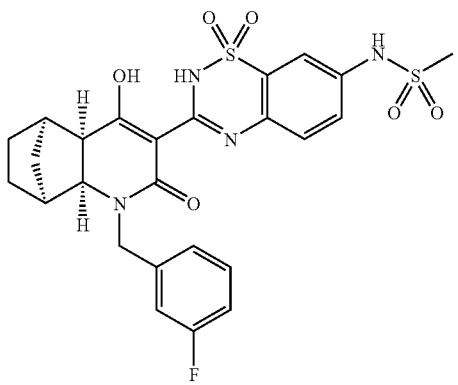

The compound of Example 30 was prepared according to the general experimental procedure A as described above.

$^1$H NMR (400 MHz, Acetone-d$_6$) δ: 1.44-1.52 (5H, m), 1.59-1.61 (1H, m), 2.80-2.82 (2H, m), 3.11 (3H, s), 3.30 (1H, d, J=10.8 Hz), 3.92 (1H, dd, J$_1$=12.6 Hz, J$_2$=3.4 Hz), 4.20 (1H, d, J=15.5 Hz), 5.32 (1H, d, J=15.8 Hz), 7.05 (1H, dt, J$_1$=8.0 Hz, J$_2$=2.7 Hz), 7.19 (1H, d, J=9.4 Hz), 7.24 (1H, d, J=7.7 Hz), 7.36-7.41 (1H, m), 7.57 (1H, d, J=9.4 Hz), 7.71 (1H, dd, J$_1$=9.6 Hz, J$_2$=2.3 Hz), 7.81 (1H, d, J=2.4 Hz). LC-MS (ESI) calcd for C$_{25}$H$_{25}$FN$_4$O$_6$S$_2$ 560.12, found 561.3 [M+H$^+$].

Biological Testing

The ability of compounds of the invention to inhibit HCV replication can be demonstrated in the following in vitro assays.

Luciferase-Based HCV Replicon Assay Protocol (EC$_{50}$ (1b))

The cell culture component of the assay is performed essentially as described by Bartenschlager et al., *Hepatology* 2002, 35, 694-703, wherein exponentially growing HCV Huh-luc/neo-ET replicon cells were seeded at 6×10$^3$ cells/well in 96 well assay plate. 24 hours later the cells were treated with various concentrations of compound or combination of compounds in triplicate using both fixed ratios and checkerboard matrices of test agents and cultured for 72 hours. The luciferase activity in the wells was determined using Bright-Glo reagent (Promega, Madison, Wis.) with a luminometer (Wallac 1420 Multilabel HTS Counter Victor 2). The background control was replicon cells treated with 100 nM BILN-2061, an inhibitor of the HCV protease. % Inhibition was determined for each compound concentration in relation to the negative (no compound) control to calculate the EC$_{50}$(1b). The compounds of Examples 1-30 each had an EC$_{50}$(1b) concentration of <0.025 uM.

Test results (EC$_{50}$(1b) values) for compound examples are summarized in Table 1, wherein ++ means HCV replicon inhibition with EC$_{50}$(1b) values less than or equal to 0.005 μM, and + means EC$_{50}$(1b) values between 0.005 μM and 0.025 μM.

TABLE 1

| Example # | EC$_{50}$ (1b) |
|---|---|
| 1 | ++ |
| 2 | ++ |
| 3 | ++ |
| 4 | ++ |
| 5 | + |
| 6 | ++ |
| 7 | ++ |
| 8 | ++ |
| 9 | ++ |
| 10 | ++ |
| 11 | ++ |
| 12 | ++ |
| 13 | ++ |
| 14 | ++ |
| 15 | + |
| 16 | + |
| 17 | + |
| 18 | + |
| 19 | + |
| 20 | + |
| 21 | + |
| 22 | + |
| 23 | + |
| 24 | + |
| 25 | + |
| 26 | + |
| 27 | + |
| 28 | + |
| 29 | + |
| 30 | + |

It is to be understood that the foregoing description is exemplary and explanatory in nature, and is intended to illustrate the invention and its preferred embodiments. Through routine experimentation, the artisan will recognize apparent modifications and variations that may be made without departing from the spirit of the invention.

What is claimed is:

1. A compound selected from
   (1R,2S,7R,8S)—N-{3-[3-(2-Chloro-4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide,
   N-{3-[(1S,2S,7R,8R)-3-(3-Chloro-4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide,
   N-{3-[(2S,7R)-6-Hydroxy-3-(3-methoxy-benzyl)-4-oxo-3-aza-tricyclo [6.2.2.0$^{2,7}$]dodec-5-en-5-yl]-1,1-dioxo-1,4-dihydro-1λ$^6$-benzo[1,2,4]thiadiazin-7-yl}-methanesulfonamide,
   N-{3-[(2S,7R)-3-(2,4-Difluoro-benzyl)-6-hydroxy-4-oxo-3-aza-tricyclo [6.2.2.0$^{2,7}$]dodec-5-en-5-yl]-1,1-dioxo-1,4-dihydro-1λ$^6$-benzo[1,2,4]thiadiazin-7-yl}-methanesulfonamide,
   N-{3-[(2S,7R)-3-(2-Chloro-4-fluoro-benzyl)-6-hydroxy-4-oxo-3-aza- tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide, N-{3-[(2S,7R)-3-(2-Bromo-benzyl)-6-hydroxy-4-oxo-3-aza-tricyclo [6.2.2.0$^{2,7}$]dodec-5-en-5-yl]-1,1-dioxo-1,4-dihydro-1λ$^6$-benzo[1,2,4]thiadiazin-7-yl}-methanesulfonamide, N-{3-[(2S,7R)-3-(4-Fluoro-3-methoxy-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide, N-{3-[(2S,7R)-3-(3-Chloro-4-fluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide, N-{3-[(2S,7R)-3-(3,3 -Dimethyl-butyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl }-methanesulfonamide, N-{3-[(2S,7R)-3-(3,4-Difluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide, N-{3-[(2S,7R)-3-(4-Fluoro-3-methyl-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide, N-{3-[2S,7R)-3-Benzyl-6-hydroxy-4-oxo-3-aza-tricyclo [6.2.2.0$^{2,7}$]dodec-5-en-5-yl]-1,1- dioxo-1,2-dihydro-1λ$^6$-benzo[1,2,4]thiadiazin-7-yl}- methanesulfonamide, (rac-di-exo, di-exo)-N-{3-[3-(4-Fluoro-benzyl)-6-hydroxy-4-oxo-3-aza-tetracyclo[6.3.1.0$^{2,7}$.0$^{9,11}$]dodec-5-en-5-yl]-1,1-dioxo-1,2-dihydro-1 X$^6$-benzo[1,2,4]thiadiazin-7-yl}-methanesulfonamide, N-{3-[(2S,7R)-3-(3-Fluoro-benzyl)-6-hydroxy-4-oxo-3-aza-tricyclo [6.2.2.0$^{2,7}$]dodec-5-en-5-yl]-1,1 -dioxo-1,2-dihydro-1λ$^6$-benzo[1,2,4]thiadiazin-7-yl}-methanesulfonamide, N-{3-[(2S,7R)-3-Cyclohexylmethyl-6-hydroxy-4-oxo-3-aza-tricyclo[6.2.2.0$^{2,7}$]dodec-5-en-5-yl]-1,1-dioxo-1,2-dihydro-1λ$^6$-benzo[1,2,4]thiadiazin-7-yl }-methanesulfonamide, N-{3-[(2S,7R)-6-Hydroxy-4-oxo-3-thiophen-2-ylmethyl-3-aza-tricyclo[6.2.2.0$^{2,7}$]dodec-5-en-5-yl]-1,1-dioxo-1,2-dihydro-1λ$^6$-benzo[1,2,4]thiadiazin-7-yl}-methanesulfonamide, N-{3-[(2S,7R)-6-Hydroxy-3-(2-methyl-benzyl)-4-oxo-3-aza-tricyclo[6.2.2.0$^{2,7}$]dodec-5-en-5-yl]-1,1-dioxo-1,2-dihydro-1λ$^6$-benzo[1,2,4]thiadiazin-7-yl}-methanesulfonamide, N-{3-[(2S,7R)-6-Hydroxy-4-oxo-3-(2,3,4-trifluoro-benzyl)-3-aza-tricyclo[6.2.2.0$^{2,7}$]dodec-5-en-5-yl]-1,1-dioxo-1,2-dihydro-1λ$^6$-benzo[1,2,4]thiadiazin-7-yl}-methanesulfonamide, N-{3-[(1S,2S,7R,8R)-3-(4-Fluoro-3-methyl-benzyl)-6-hydroxy-4-oxo-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide, N-{3-[(1S,2S,7R,8R)-(3-Benzyl-6-hydroxy-4-oxo-3-aza-tricyclo [6.2.1.0$^{2,7}$]undec-5-en-5-yl]-1,1-dioxo-1,2-dihydro-1λ$^6$-benzo[1,2,4]thiadiazin-7-yl}-methanesulfonamide, N-{3-[(1R,2S,7R,8S)-3-(3-Fluoro-benzyl)-6-hydroxy-4-oxo-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide, N-{3-[(1 S,2S,7R,8R)-6-Hydroxy-4-oxo-3-(1 -trifluoromethyl-cyclopropylmethyl)-3-aza-tricyclo [6.2.1.0$^{2,7}$]undec-5-en-5-yl]-1,1-dioxo-1,2-dihydro-1λ$^6$-benzo[1,2,4]thiadiazin-7-yl}-methanesulfonamide, N-{3-[(1S,2S,7R,8R)-3-(3,4-Difluoro-benzyl)-6-hydroxy-4-oxo-3-aza-tricyclo[6.2.1.0$^{2,7}$]undec-5-en-5-yl]-1,1-dioxo-1,2-dihydro-1λ$^6$-benzo[1,2,4thiadiazin-7-yl}-methanesulfonamide, N-{3-[(1R,2S,7R,8S)-6-Hydroxy-4-oxo-3-(2,3,4-trifluoro-benzyl)-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide, N-{3-[(1R,2S,7R,8S)-6-Hydroxy-4-oxo-3-thiophen-3-ylmethyl-3-aza-tricyclo[6.2.1.0$^{2,7}$]undec-5-en-5-yl]-1,1 -dioxo-1,2-dihydro-1λ$^6$-benzo[1,2,4]thiadiazin-7-yl}-methanesulfonamide, N-{3-[(2S,7R)-6-Hydroxy-4-oxo-3-(2,4,5-trifluoro-benzyl)-3-aza-tricyclo[6.2.2.0$^{2,7}$]dodec-5-en-5-yl]-1,1-dioxo-1,2-dihydro-1λ$^6$-benzo[1,2,4]thiadiazin-7-yl}-methanesulfonamide, N-{3-[(1R,2S,7R,8S)-6-Hydroxy-4-oxo-3-thiophen-2-ylmethyl-3-aza-tricyclo [6.2. 1 .0$^{2,7}$]undec-5-en-5-yl]-1,1-dioxo-1,2-dihydro-1λ2$^6$-benzo[1,2,4]thiadiazin-7-yl}-methanesulfonamide, N-{3-[(1R,2S,7R,8S)-(3-Cyclohexylmethyl-6-hydroxy-4-oxo-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide, N-{3-[(1 S,2S,7R,8R)-6-Hydroxy-3-(2-methyl-benzyl)-4-oxo-3-aza-tricyclo [6.2.1.0$^{2,7}$]undec-5-en-5-yl]-1,1 -dioxo-1,2-dihydro-1 2$^6$-benzo[1,2,4]thiadiazin-7-yl}-methanesulfonamide, and N-{3-[(1S,2S,7R,8R)-3-(3-Fluoro-benzyl)-6-hydroxy-4-oxo-3-aza-tricyclo[6.2.1.0$^{2,7}$]undec-5-en-5-yl]-1,1-dioxo-1,2-dihydro-1λ$^6$-benzo[1,2,4]thiadiazin-7-yl}-methanesulfonamide, or pharmaceutically acceptable salts thereof.

2. The compound of claim 1 selected from (1 R,2S,7R,8S)-N-{3-[3-(2-Chloro-4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide, N-{3-[(2S,7R)-3-(2-Chloro-4-fluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide, N-{3-[(2S,7R)-3-(4-Fluoro-3-methoxy-benzyl)-6-hydroxy-4-oxo-3-aza-tricyclo [6.2.2.0$^{2,7}$]dodec-5-en-5-yl]-1,1-dioxo-1,4-dihydro-1λ$^6$-benzo[1,2,4]thiadiazin-7-yl}-methanesulfonamide, N-{3-[(2S,7R)-3-(3-Chloro-4-fluoro-benzyl)-6-hydroxy-4-oxo-3-aza-tricyclo[6.2.2.0$^{2,7}$]dodec-5-en-5-yl]-1,1-dioxo-1,4-dihydro-λ$^6$-benzo[1,2,4]thiadiazin-7-yl}-methanesulfonamide, N-{3-[(2S,7R)-3-(3 ,4-Difluoro-benzyl)-6-hydroxy-4-oxo-3-aza-tricyclo [6.2.2.0$^{2,7}$]dodec-5-en-5-yl]-1,1-dioxo-1,4-dihydro-1λ$^6$-benzo[1,2,4]thiadiazin-7-yl}-methanesulfonamide, N-{3-[(2S,7R)-3-(4-Fluoro-3-methyl-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide, and (rac-di-exo, di-exo)-N-{3-[3-(4-Fluoro-benzyl)-6-hydroxy-4-oxo-3-aza-tetracyclo[6.3.1.0$^{2,7}$.0$^{9,11}$]dodec-5-en-5-yl]-1,1-dioxo-1,2-dihydro-1λ$^6$-benzo[1,2,4]thiadiazin-7-yl}-methanesulfonamide, or pharmaceutically acceptable salts thereof.

3. The compounds of claim 1 selected from
(1R,2S,7R,8S)-N-{3-[3-(2-Chloro-4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide, and
N-{3-[(2S,7R)-3-(3,4-Difluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide, or pharmaceutically acceptable salts thereof.

4. A pharmaceutically acceptable composition comprising a compound of claim 1, or a pharmaceutically acceptable salt thereof, and a pharmaceutically acceptable carrier.

5. A method for treating hepatitis C virus infection in a mammal in need thereof, comprising administering to the mammal a therapeutically effective amount of a compound of claim 1.

6. The method of claim 5 wherein the mammal is a human.

\* \* \* \* \*